United States Patent
Wittliff, III et al.

(10) Patent No.: US 9,081,883 B2
(45) Date of Patent: *Jul. 14, 2015

(54) DYNAMIC DECISION SEQUENCING METHOD AND APPARATUS FOR OPTIMIZING A DIAGNOSTIC TEST PLAN

(71) Applicant: Service Solutions U.S. LLC, Warren, MI (US)

(72) Inventors: William W. Wittliff, III, Gobles, MI (US); Olav M. Underdal, Kalamazoo, MI (US); Harry M. Gilbert, Portage, MI (US); Alex Portyanko, Portage, MI (US)

(73) Assignee: Bosch Automotive Service Solutions Inc., Warren, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/785,729

(22) Filed: Mar. 5, 2013

(65) Prior Publication Data

US 2013/0185093 A1 Jul. 18, 2013

Related U.S. Application Data

(63) Continuation-in-part of application No. 11/452,250, filed on Jun. 14, 2006, now Pat. No. 8,423,226.

(51) Int. Cl.
*G06F 19/00* (2011.01)
*G06N 7/00* (2006.01)

(52) U.S. Cl.
CPC .............. *G06F 19/345* (2013.01); *G06N 7/005* (2013.01)

(58) Field of Classification Search
CPC ............ G06F 19/3418; G06F 19/3443; G06F 19/3487; G06Q 50/24
USPC ...................................... 700/90, 93; 705/2, 3
See application file for complete search history.

(56) References Cited

U.S. PATENT DOCUMENTS

| 4,404,639 A | 9/1983 | McGuire et al. |
| 4,757,463 A | 7/1988 | Ballou et al. |

(Continued)

FOREIGN PATENT DOCUMENTS

| CN | 1527934 A | 9/2004 |
| DE | 10233503 A1 | 2/2004 |

(Continued)

OTHER PUBLICATIONS

European Search Report for Appl. No. 07252442.4, dated Sep. 11, 2007.

(Continued)

*Primary Examiner* — Khoi Tran
*Assistant Examiner* — Jorge Peche
(74) *Attorney, Agent, or Firm* — Baker & Hostetler LLP

(57) ABSTRACT

A dynamic diagnostic plan generator arranges diagnostic test procedures related to a vehicle/power tool/patient symptom or operational problem in a sequence based on a probabilistic Failure Mode and Effects Analysis (FMEA). The diagnostic plan generator also tracks a vehicle/power tool/patient state, and provides instructions for test preparation steps and instructions for performing the diagnostic test procedures. The plan generator further generates schematic illustrations of the diagnostic test procedures, and creates a diagnostic data structure containing information related to the diagnostic test procedures. In addition, the diagnostic plan generator sends and receives information regarding actual failure mode occurrences, for example, to and from a central database. Furthermore, the diagnostic plan generator facilitates the creation of failure mode tests by an expert diagnostics author.

20 Claims, 12 Drawing Sheets

(56) References Cited

U.S. PATENT DOCUMENTS

| | | |
|---|---|---|
| 4,796,206 A | 1/1989 | Boscove et al. |
| 4,817,092 A | 3/1989 | Denny |
| 4,866,635 A | 9/1989 | Kahn et al. |
| 4,873,687 A | 10/1989 | Breu |
| 4,881,230 A | 11/1989 | Clark et al. |
| 4,943,919 A | 7/1990 | Aslin et al. |
| 4,954,964 A | 9/1990 | Singh |
| 4,964,125 A | 10/1990 | Kim |
| 4,985,857 A | 1/1991 | Bajpai et al. |
| 5,010,487 A | 4/1991 | Stonehocker |
| 5,023,791 A | 6/1991 | Herzberg et al. |
| 5,025,392 A | 6/1991 | Singh |
| 5,036,479 A | 7/1991 | Prednis et al. |
| 5,099,436 A | 3/1992 | McCown et al. |
| 5,109,380 A | 4/1992 | Ogino |
| 5,111,402 A | 5/1992 | Brooks et al. |
| 5,127,005 A | 6/1992 | Oda et al. |
| 5,161,158 A | 11/1992 | Chakravarty et al. |
| 5,184,312 A | 2/1993 | Ellis |
| 5,214,577 A | 5/1993 | Sztipanovits et al. |
| 5,270,920 A | 12/1993 | Pearse et al. |
| 5,293,323 A | 3/1994 | Doskocil et al. |
| 5,396,422 A | 3/1995 | Forchert et al. |
| 5,442,549 A | 8/1995 | Larson |
| 5,491,631 A | 2/1996 | Shirane et al. |
| 5,524,078 A | 6/1996 | Kolb et al. |
| 5,541,840 A | 7/1996 | Gurne et al. |
| 5,561,762 A | 10/1996 | Smith et al. |
| 5,572,424 A | 11/1996 | Kellogg et al. |
| 5,586,252 A | 12/1996 | Barnard et al. |
| 5,617,039 A | 4/1997 | Kuck et al. |
| 5,631,831 A | 5/1997 | Bird et al. |
| 5,670,939 A | 9/1997 | Rodewald et al. |
| 5,671,141 A | 9/1997 | Smith et al. |
| 5,696,676 A | 12/1997 | Takaba |
| 5,729,452 A | 3/1998 | Smith et al. |
| 5,742,500 A | 4/1998 | Irvin |
| 5,778,381 A | 7/1998 | Sandifer |
| 5,835,871 A | 11/1998 | Smith et al. |
| 5,838,261 A | 11/1998 | Lauta et al. |
| 5,852,789 A | 12/1998 | Trsar et al. |
| 5,883,586 A | 3/1999 | Tran et al. |
| 5,916,286 A | 6/1999 | Seashore et al. |
| 5,964,811 A | 10/1999 | Ishii et al. |
| 5,964,813 A | 10/1999 | Ishii et al. |
| 5,987,443 A | 11/1999 | Nichols et al. |
| 6,003,021 A | 12/1999 | Zadik et al. |
| 6,003,808 A | 12/1999 | Nguyen et al. |
| 6,006,146 A | 12/1999 | Usui et al. |
| 6,012,152 A | 1/2000 | Douik et al. |
| 6,032,088 A | 2/2000 | Feldmann et al. |
| 6,041,287 A | 3/2000 | Dister et al. |
| 6,055,468 A | 4/2000 | Kaman et al. |
| 6,064,998 A | 5/2000 | Zabloudil et al. |
| 6,067,537 A | 5/2000 | O'Connor et al. |
| 6,067,538 A | 5/2000 | Zorba et al. |
| 6,073,127 A | 6/2000 | Lannert et al. |
| 6,085,184 A | 7/2000 | Bertrand et al. |
| 6,119,074 A | 9/2000 | Sarangapani |
| 6,122,575 A | 9/2000 | Schmidt et al. |
| 6,134,488 A | 10/2000 | Sasaki et al. |
| 6,141,608 A | 10/2000 | Rother |
| 6,167,352 A | 12/2000 | Kanevsky et al. |
| 6,175,787 B1 | 1/2001 | Breed |
| 6,192,302 B1 | 2/2001 | Giles et al. |
| 6,205,465 B1 | 3/2001 | Schoening et al. |
| 6,226,627 B1 | 5/2001 | Polak |
| 6,236,917 B1 | 5/2001 | Liebl et al. |
| 6,249,755 B1 | 6/2001 | Yemini et al. |
| 6,263,268 B1 | 7/2001 | Nathanson |
| 6,263,322 B1 | 7/2001 | Kirkevold et al. |
| 6,282,469 B1 | 8/2001 | Rogers et al. |
| 6,301,531 B1 | 10/2001 | Pierro et al. |
| 6,314,375 B1 | 11/2001 | Sasaki et al. |
| 6,330,499 B1 | 12/2001 | Chou et al. |
| 6,338,148 B1 | 1/2002 | Gillenwater et al. |
| 6,363,304 B1 | 3/2002 | Ramsey |
| 6,370,455 B1 | 4/2002 | Larson et al. |
| 6,434,455 B1 | 8/2002 | Snow et al. |
| 6,477,453 B2 | 11/2002 | Oi et al. |
| 6,493,615 B1 | 12/2002 | Johnston |
| 6,505,106 B1 | 1/2003 | Lawrence et al. |
| 6,512,968 B1 | 1/2003 | de Bellefeuille et al. |
| 6,522,987 B1 | 2/2003 | Flink et al. |
| 6,526,340 B1 | 2/2003 | Reul et al. |
| 6,526,361 B1 | 2/2003 | Jones et al. |
| 6,538,472 B1 | 3/2003 | McGee |
| 6,557,115 B2 | 4/2003 | Gillenwater et al. |
| 6,560,516 B1 | 5/2003 | Baird et al. |
| 6,574,537 B2 | 6/2003 | Kipersztok et al. |
| 6,591,182 B1 | 7/2003 | Cece et al. |
| 6,609,051 B2 | 8/2003 | Fiechter et al. |
| 6,611,740 B2 | 8/2003 | Lowrey et al. |
| 6,615,120 B1 | 9/2003 | Rother |
| 6,636,790 B1 | 10/2003 | Lightner et al. |
| 6,640,166 B2 | 10/2003 | Liebl et al. |
| 6,643,607 B1 | 11/2003 | Chamberlain et al. |
| 6,652,169 B2 | 11/2003 | Parry |
| 6,662,087 B1 | 12/2003 | Liebl et al. |
| 6,694,235 B2 | 2/2004 | Akiyama |
| 6,708,092 B1 | 3/2004 | Starks et al. |
| 6,711,134 B1 | 3/2004 | Wichelman et al. |
| 6,714,846 B2 | 3/2004 | Trsar et al. |
| 6,738,697 B2 | 5/2004 | Breed |
| 6,748,304 B2 | 6/2004 | Felke et al. |
| 6,751,536 B1 | 6/2004 | Kipersztok et al. |
| 6,768,935 B1 | 7/2004 | Morgan et al. |
| 6,795,778 B2 | 9/2004 | Dodge et al. |
| 6,807,469 B2 | 10/2004 | Funkhouser et al. |
| 6,819,988 B2 | 11/2004 | Dietz et al. |
| 6,836,708 B2 | 12/2004 | Tripathi |
| 6,845,307 B2 | 1/2005 | Rother |
| 6,845,468 B2 | 1/2005 | James |
| 6,868,319 B2 | 3/2005 | Kipersztok et al. |
| 6,874,680 B1 | 4/2005 | Klaus et al. |
| 6,928,349 B1 | 8/2005 | Namaky et al. |
| 6,941,203 B2 | 9/2005 | Chen |
| 6,950,829 B2 | 9/2005 | Schlabach et al. |
| 6,993,421 B2 | 1/2006 | Pillar et al. |
| 7,010,460 B2 | 3/2006 | Trsar et al. |
| 7,013,411 B2 | 3/2006 | Kallela et al. |
| 7,050,894 B2 | 5/2006 | Halm et al. |
| 7,062,622 B2 | 6/2006 | Peinado |
| 7,073,120 B2 | 7/2006 | Torii et al. |
| 7,082,359 B2 | 7/2006 | Breed |
| 7,103,610 B2 | 9/2006 | Johnson et al. |
| 7,103,679 B2 | 9/2006 | Bonn |
| 7,120,559 B1 | 10/2006 | Williams et al. |
| 7,120,890 B2 | 10/2006 | Urata et al. |
| 7,124,058 B2 | 10/2006 | Namaky et al. |
| 7,142,960 B2 | 11/2006 | Grier et al. |
| 7,162,741 B2 | 1/2007 | Eskin et al. |
| 7,165,216 B2 | 1/2007 | Chidlovskii et al. |
| 7,171,372 B2 | 1/2007 | Daniel et al. |
| 7,203,881 B1 | 4/2007 | Williams et al. |
| 7,209,815 B2 | 4/2007 | Grier et al. |
| 7,209,817 B2 | 4/2007 | Abdel-Malek et al. |
| 7,209,860 B2 | 4/2007 | Trsar et al. |
| 7,216,052 B2 | 5/2007 | Fountain et al. |
| 7,251,535 B2 | 7/2007 | Farchmin et al. |
| 7,272,475 B2 | 9/2007 | Gawlik et al. |
| 7,272,756 B2 | 9/2007 | Brink et al. |
| 7,286,047 B2 | 10/2007 | Oesterling et al. |
| 7,373,225 B1 | 5/2008 | Grier et al. |
| 7,376,497 B2 | 5/2008 | Chen |
| 7,379,846 B1 | 5/2008 | Williams et al. |
| 7,400,954 B2 | 7/2008 | Sumcad et al. |
| 7,409,317 B2 | 8/2008 | Cousin et al. |
| 7,428,663 B2 | 9/2008 | Morton et al. |
| 7,430,535 B2 | 9/2008 | Dougherty et al. |
| 7,444,216 B2 | 10/2008 | Rogers et al. |
| 7,483,774 B2 | 1/2009 | Grichnik et al. |
| 7,555,376 B2 | 6/2009 | Beronja |
| 7,565,333 B2 | 7/2009 | Grichnik et al. |

(56) References Cited

U.S. PATENT DOCUMENTS

| | | | |
|---|---|---|---|
| 7,610,127 B2 | 10/2009 | D'Silva et al. | |
| 7,636,622 B2 | 12/2009 | Underdal et al. | |
| 7,643,912 B2 | 1/2010 | Heffington | |
| 7,643,916 B2 | 1/2010 | Underdal et al. | |
| 7,647,349 B2 | 1/2010 | Hubert et al. | |
| 7,715,961 B1 | 5/2010 | Kargupta | |
| 7,739,007 B2 | 6/2010 | Logsdon | |
| 7,751,955 B2 | 7/2010 | Chinnadurai et al. | |
| 7,752,224 B2 | 7/2010 | Davis et al. | |
| 7,761,591 B2 | 7/2010 | Graham | |
| 7,765,040 B2 | 7/2010 | Underdal et al. | |
| 7,778,746 B2 | 8/2010 | McLeod et al. | |
| 7,788,096 B2 | 8/2010 | Chelba et al. | |
| 7,809,482 B2 | 10/2010 | Bertosa et al. | |
| 7,853,435 B2 | 12/2010 | Dodge et al. | |
| 7,860,620 B2 | 12/2010 | Kojitani et al. | |
| 7,865,278 B2 | 1/2011 | Underdal et al. | |
| 7,882,394 B2 | 2/2011 | Hosek et al. | |
| 7,925,397 B2 | 4/2011 | Underdal et al. | |
| 8,005,627 B2 * | 8/2011 | Porwancher | 702/20 |
| 8,019,501 B2 | 9/2011 | Breed | |
| 8,024,083 B2 | 9/2011 | Chenn | |
| 8,055,907 B2 | 11/2011 | Deem et al. | |
| 8,239,094 B2 | 8/2012 | Underdal et al. | |
| 8,463,623 B2 * | 6/2013 | Ware et al. | 705/3 |
| 8,478,534 B2 * | 7/2013 | Zhu et al. | 702/19 |
| 2002/0007237 A1 | 1/2002 | Phung et al. | |
| 2002/0059075 A1 | 5/2002 | Schick et al. | |
| 2002/0091736 A1 | 7/2002 | Wall | |
| 2002/0112072 A1 | 8/2002 | Jain | |
| 2002/0116669 A1 | 8/2002 | Jain | |
| 2002/0173885 A1 | 11/2002 | Lowrey et al. | |
| 2003/0177414 A1 | 9/2003 | Pillutla et al. | |
| 2004/0001106 A1 | 1/2004 | Deutscher et al. | |
| 2004/0039493 A1 | 2/2004 | Kaufman | |
| 2004/0181688 A1 | 9/2004 | Wittkotter | |
| 2005/0022168 A1 * | 1/2005 | Zhu et al. | 717/124 |
| 2005/0043868 A1 | 2/2005 | Mitcham | |
| 2005/0065678 A1 | 3/2005 | Smith et al. | |
| 2005/0071143 A1 | 3/2005 | Tran et al. | |
| 2005/0137762 A1 | 6/2005 | Rother | |
| 2005/0144183 A1 | 6/2005 | McQuown et al. | |
| 2005/0177352 A1 | 8/2005 | Gravel | |
| 2005/0222718 A1 | 10/2005 | Lazarz et al. | |
| 2006/0030981 A1 | 2/2006 | Robb et al. | |
| 2006/0074824 A1 | 4/2006 | Li | |
| 2006/0095230 A1 | 5/2006 | Grier et al. | |
| 2006/0129906 A1 | 6/2006 | Wall | |
| 2006/0136104 A1 | 6/2006 | Brozovich et al. | |
| 2006/0142907 A1 | 6/2006 | Cancilla et al. | |
| 2006/0142910 A1 | 6/2006 | Grier et al. | |
| 2006/0149434 A1 | 7/2006 | Bertosa et al. | |
| 2006/0210141 A1 | 9/2006 | Kojitani et al. | |
| 2006/0229777 A1 | 10/2006 | Hudson et al. | |
| 2007/0100520 A1 | 5/2007 | Shah et al. | |
| 2007/0124282 A1 | 5/2007 | Wittkotter | |
| 2007/0226540 A1 | 9/2007 | Konieczny | |
| 2007/0250228 A1 | 10/2007 | Reddy et al. | |
| 2007/0293998 A1 | 12/2007 | Underdal et al. | |
| 2007/0294001 A1 | 12/2007 | Underdal et al. | |
| 2008/0064118 A1 * | 3/2008 | Porwancher | 436/513 |
| 2009/0216584 A1 | 8/2009 | Fountain et al. | |
| 2009/0271066 A1 | 10/2009 | Underdal et al. | |
| 2010/0082197 A1 | 4/2010 | Kolbet et al. | |
| 2010/0262431 A1 | 10/2010 | Gilbert | |
| 2011/0112852 A1 * | 5/2011 | Ware et al. | 705/2 |
| 2011/0161104 A1 * | 6/2011 | Gilbert et al. | 705/2 |

FOREIGN PATENT DOCUMENTS

| | | |
|---|---|---|
| DE | 10332203 A1 | 2/2005 |
| EP | 1674958 A1 | 6/2006 |
| GB | 2329943 A | 4/1999 |
| JP | H03-087671 A | 4/1991 |
| JP | 06-265596 A1 | 9/1994 |
| JP | H08-043265 A | 2/1996 |
| JP | H10-253504 A | 9/1998 |
| JP | 2001-202125 A | 7/2001 |
| JP | 2001-229299 A | 8/2001 |
| JP | 2002-183334 A | 6/2002 |
| JP | 2004-299587 A | 10/2004 |
| JP | 2007-326425 A | 12/2007 |

OTHER PUBLICATIONS

European Search Report for Appl. No. 07252441, dated Jun. 20, 2008.
L.J. Aartman, et al., "An Independent Verification Tool for Multi-Vendor Mode S Airborne Transponder Conformance Testing," 21st Digital Avionics Systems Conference, 2002, pp. 12.E.5-1-12.E.5-11, vol. 2.
"Annex A Test Bit Sequence," Methodology for Jitter and Signal Quality; Specification-MJSQ Technical Report REV 10.0, pp. 117-132, Mar. 10, 2003.
Tariq Assaf, et al. "Automatic Generation of Diagnostic Expert Systems from Fault Trees," 2003 Proceedings Annual Reliability & Maintainability Symposium, pp. 143-147.
R. Belhassine-Cherif, et al., "Multiple Fault Diagnostics for Communicating Nondeterministic Finite State Machines," 6th IEEE Symposium on Computers and Communications, Jul. 3-5, 2001, pp. 661-666.
M. Ben-Bassat, et al., "A1-Test: A Real Life Expert System for Electronic Troubleshooting (A Description and a Case Study)," 4th Conference on Artificial Intelligence Applications, 1988, pp. 2-10.
F. Brajou, et al., "The Airbus A380—An AFDX-Based Flight Test Computer Concept," 2004 IEEE Autotestcon, pp. 460-463.
Cantone, et al., "IN-ATE: Fault Diagnosis as Expert System Guided Search," Computer Expert Systems, L. Bolc & M.J. Coombs (eds.), Springer-Verlag, New York 1986, pp. 298-348.
"Computerized Diagnostic Tester at Hand," Electrical World, Aug. 1, 1975, pp. 36-38.
T.A. Cross, "A Digital Electronic System for Automobile Testing and Diagnosis," IEE Conference Jul. 6-9, 1976, London, England, pp. 152-159.
eHow Contributor, "How to Organize Computer Files," printed Mar. 31, 2011 from http://www.ehow.com/print/how_138482_organize-computer-files.html.
F. Esposito, et al., "Machine Learning Methods for Automatically Processing Historical Documents: from Paper Acquisition to XML Transformation," 1st Int'l Workshop on Document Image Analysis for Libraries, Jan. 23-24, 2004, pp. 328-335.
H. Garcia-Molina, et al., "dSCAM: Finding Document Copies Across Multiple Databases," 4th Int'l Conference on Parallel and Distributed Information Systems, Dec. 18-20, 1996, pp. 68-79.
I. Ghosh, et al., "Automatic Test Pattern Generation for Functional Register-Transfer Level Circuits Using Assignment Decision Diagrams," IEEE Transactions on Computer-Aided Design of Integrated Circuits and Systems, vol. 20, Issue 3, Mar. 2001, pp. 402-415.
M. Koppel, et al., "Automatically Classifying Documents by Ideological and Organizational Affiliation," IEEE Int'l Conference on Intelligence and Security Informatics, Jun. 8-11, 2009, pp. 176-178.
J.C. Lin, et al., "Using Genetic Algorithms for Test Case Generation in Path Testing," 9th Asian Test Symposium, Dec. 4-6, 2000, pp. 241-246.
W. Linzhang, et al., "Generating Test Cases from UML Activity Diagram Based on Gray-Box Method," 11th Asia-Pacific Software Engineering Conference, Nov. 30-Dec. 3, 2004, pp. 1-8.
B.D. Liu, et al., "Efficient Global Strategy for Designing and Testing Scanned Sequential Circuits," IEE Proceedings on Computers and Digital Techniques, vol. 142, No. 2, Mar. 1995, pp. 170-176.
M. Mayer, "The Computerized Diagnostic Rhyme Test as a Design Tool for Armored Vehicle Intercommunications Systems," Military Communications Conference, 1985, pp. 166-170.
Microsoft at Work, "File Organization tips: 9 ideas for managing files and folders," printed Mar. 30, 2011 from http://www.microsoft.com/atwork/productivity/files.aspx.
S.M. Namburu, et al., "Systematic Data-Driven Approach to Real-Time Fault Detection and Diagnosis in Automotive Engines," 2006

(56) References Cited

OTHER PUBLICATIONS

IEEE AUTOTESTCON, pp. 59-65.

"Names files and folders—How to—Web Team—University of Canterbury, New Zealand," printed on Mar. 31, 2011 from http://www.canterbury.ac.nz/web/how/filename.shtml.

D. Niggemeyer, et al., "Automatic Generation of Diagnostic March Tests," 19th IEEE Proceedings on VLSI Test Symposium, 2001, pp. 299-304.

Yiannis Papadopoulos, et al., "Automating the Failure Modes and Effects Analysis of Safety Critical Systems," Proceedings of the Eighth IEEE Int'l Symposium on High Assurance Systems Engineering (HASE '04), 2004.

F.C. Pembe, et al., "Heading-Based Sectional Hierarchy Identification for HTML Documents," 22nd Int'l Symposium on Computer and Information Sciences, Nov. 7-9, 2007, pp. 1-6.

F. Pipitone, "The FIS Electronics Troubleshooting System Guided Search," Computer Expert Systems, vol. 19, No. 7, 1986, pp. 68-76.

G. Qin, et al., "On-Board Fault Diagnosis of Automated Manual Transmission Control System," IEEE Transactions on Control Systems Technology, vol. 12, No. 4, Jul. 2004, pp. 564-568.

H.M.T. Saarikoski, "2T: Two-Term Indexing of Documents Using Syntactic and Semantic Constraints," 16th Int'l Workshop on Database and Expert Systems Applications, Aug. 22-26, 2005, pp. 1025-1028.

P. Samuel, et al., "UML Sequencing Diagram Based Testing Using Slicing," An Int'l Conference of IEEE India Council, Dec. 11-13, 2005, pp. 176-178.

F.Y. Shih, et al., "A Document Segmentation, Classification and Recognition System," 2nd Int'l Conference on Systems Integration, 1992, pp. 258-267.

Genichi Taguchi, et al., The Mahalanobis-Taguchi System. Published 2000, McGraw-Hill Professional. http://books.google.com/books?id=5AOuyyccV8kC&printsec=frontcover&sig=WdZNGINfzuveQpcYASuCMCvuiO (no hard copy, unable to print, must review on-line).

H. Trier, "Further Development of the Periodical Vehicle Test by Using Diagnostic Interface," IEE Colloquium on Vehicle Diagnostics in Europe, 1994, pp. 4/1-4/2.

J. van Beers, et al., "Test Features of a Core-Based Co-Processor Array for Video Applications," Int'l Test Conference, 1999, pp. 638-647.

J.R. Wagner, "Failure Mode Testing Tool Set for Automotive Electronic Controllers," IEEE Transactions on Vehicular Technology, vol. 43, Issue 1, Feb. 1994, pp. 156-163.

Reuben Wright, et al., "How Can Ontologies Help Repair Your Car?" XTECH 2005: XML, the Web and beyond; May 27, 2005, Amsterdam; http://ww.idealliance.org/proceedings/xtech05/papers/02-07-02/.

B. Ives et al., After the Sale: Leveraging Maintenance with Information Technology, MIS Quarterly, vol. 12, No. 1, Mar. 1988, pp. 7-21.

Volkswagon-Audi Vehicle Communication Software Manual, Snap-On, published Mar. 31, 2006, http://www.w124performance.com/docs/general/Snap-On/manuals/VCS_Manual_VW_Audi.pdf, XP007920392.

* cited by examiner

Test Preparation Steps

- ✓ Disconnect TPS
- ▶ Disconnect ECM
- ✓ Connect VOM
  - Set VOM to Ohms
- ✓ Put Socket Probe on VOM Red Lead
- ✓ Put Socket Probe on VOM Black Lead

Test Steps

- ✓ Terminal A wire Shorted to Battery Volts Test
- ▶ Terminal C Wire Continuity Test
-   Terminal B wire Shorted to Volts Test
-   Throttle Position Sensor Test
-   Terminal A wire Shorted to B wire Test

| Description | Information | Wiring |

The ECM supplies a 5 volt signal (Pin gray 1) and a sensor ground (Pin gray 7) to the throttle position sensor (TP sensor). The TP sensor returns a signal to the ECM (Pin gray 2). The returned signal varies in voltage according to throttle position. The output signal from the TP sensor varies from 0.5-1.5 volts at idle (closed throttle) to 3.9-4.9 volts at wide open throttle.

| Results | Wiring |

Circuit between
TP Sensor [88A] terminal "B" and      58
ECM [11B] Gray terminal "2" (V/Y wire)
is shorted to the circuit between
TP Sensor [88A] terminal "A" and
ECM [11B] Gray terminal "1" (R/W wire)

Restore Connections, Perform Suggested Repairs,    60
Clear DTCs, and Verify Repairs

62

Cancel    <Back                                Log Test

FIG. 8

TEST PREPARATION STEPS

- ☑ TURN ON HEART MONITOR
- ☑ TURN OFF BLOOD PRESSURE MONITOR
- ☑ CONNECT TEST PROBES TO PATIENT
- ☑ CONNECT OXYGEN SUPPLY TO PATIENT

TEST STEPS

- ☑ ACTIVATE TEST PROBES
- ▶ MONITOR VITAL SIGNS
  TRANSMIT TEST SIGNALS
  DETECT CHANGES IN PATIENT
  RECORD TEST RESULTS

DYNAMIC DECISION SEQUENCING METHOD AND APPARATUS FOR OPTIMIZING A DIAGNOSTIC TEST PLAN

CROSS-REFERENCE TO RELATED APPLICATIONS

This application claims priority to and is a continuation-in-part of U.S. patent application Ser. No. 11/452,250, entitled "Dynamic Decision Sequencing Method and Apparatus for Optimizing a Diagnostic Test Plan," filed on Jun. 14, 2006, which is hereby incorporated by reference herein in its entirety.

FIELD OF THE INVENTION

The present invention relates generally to diagnostic equipment. More particularly, the present invention relates to the generation of optimized diagnostic test plans, such as medical diagnostic tests and diagnostic systems of various industries.

BACKGROUND OF THE INVENTION

Diagnostic systems are used by technicians and professionals in virtually all industries to perform basic and advanced system testing functions. For example, in the power tool, appliance, automotive, trucking, heavy equipment and aircraft industries, diagnostic test systems provide for vehicle onboard computer fault or trouble code display, interactive diagnostics, multiscope and multimeter functions, and electronic service manuals. In the medical industry, diagnostic systems provide for monitoring body functions and diagnosis of medical conditions, as well as system diagnostics to detect anomalies in the medical equipment.

In many industries, diagnostic systems play an increasingly important role in manufacturing processes, as well as in maintenance and repair throughout the lifetime of the equipment or product. Some diagnostic systems are based on personal computer technology and feature user-friendly, menu-driven diagnostic applications. These systems assist technicians and professionals at all levels in performing system diagnostics on a real-time basis.

A typical diagnostic system includes a display on which instructions for diagnostic procedures are displayed. The system also includes a system interface that allows the operator to view real-time operational feedback and diagnostic information. Thus, the operator may view, for example, vehicle engine speed in revolutions per minute, or battery voltage during start cranking; revolution per minute (RPM) for power tool such as a band saw or a patient's heartbeat rate or blood pressure. With such a system, a relatively inexperienced operator may perform advanced diagnostic procedures and diagnose complex operational or medical problems.

The diagnostic procedures for diagnostic systems of this sort are typically developed by experienced technical experts or professionals. The technical expert or professional provides the technical experience and knowledge required to develop complex diagnostic procedures. Thus, the efficacy of the diagnostic procedures, in particular the sequence in which the diagnostic procedures are performed, is highly dependent on the expertise of the technical expert or professional authoring the procedures.

Thus, existing diagnostic systems have a disadvantage in that the sequence of execution of diagnostic procedures is highly dependent upon the expertise of the technical experts and professionals who author the diagnostic procedures. The technical experts and professionals often do not have access to complete information regarding historical outcomes of diagnostic testing that has been performed, and in particular, statistical information regarding the historical outcomes of diagnostic testing. As a result, diagnostic testing can consume unnecessary time and cost, because it is based on incomplete information. Accordingly, it is desirable to provide a method and apparatus for generating an optimized diagnostic test plan that can be executed on diagnostic systems of various industries.

SUMMARY OF THE INVENTION

The foregoing needs are met, to a great extent, by the present invention, wherein in one aspect an apparatus and method are provided that in some embodiments provide for generating an optimized diagnostic test plan that can be executed on a diagnostic system.

In accordance with one embodiment of the present invention, a computer-implemented method of dynamically producing a diagnostic test procedure sequence to diagnose a disease or disorder of a patient is provided. The computer-implemented method includes selecting a first plurality of diagnostic test procedures related to a symptom exhibited by the patient, arranging an order of the first plurality of diagnostic test procedures based on a probabilistic disease or disorder analysis and time required to perform each of the first plurality of diagnostic test procedures, formatting a step of a first diagnostic test procedure from among the first plurality of diagnostic test procedures for display on a display device, displaying the formatted step on the display device, arranging an order of a second plurality of diagnostic test procedures, which includes one diagnostic test procedure of the first plurality of diagnostic test procedures, during execution of the first plurality of diagnostic test procedures, and based on intermediate diagnostic test information obtained from execution of the first diagnostic test procedure, and displaying a step of a second diagnostic test procedure from among the second plurality of diagnostic test procedures on the display device, wherein each of the above steps is performed by a computer.

In accordance with another embodiment of the present invention a diagnostic tool for dynamically producing a diagnostic test sequence to diagnose a disease or disorder of a patient is provided. The diagnostic tool includes a sequence optimizing module, including a processor and configured to arrange an order of a first plurality of diagnostic test procedures based on a probabilistic disease or disorder analysis and time required to perform each of the first plurality of diagnostic test procedures, a display device; and a display module configured to format a step of a first diagnostic test procedure from among the first plurality of diagnostic test procedures for display on the display device; wherein the sequence optimizing module is further configured to arrange an order of a second plurality of diagnostic test procedures, which includes one diagnostic test procedure of the first plurality of diagnostic test procedures, during execution of the first plurality of diagnostic test procedures, and based on intermediate diagnostic test information obtained from execution of the first plurality of diagnostic test procedures; and wherein the display module is further configured to format a step of a second diagnostic test procedure from among the second plurality of diagnostic test procedures for display on the display device.

In accordance with yet another embodiment of the present invention, a computer-implemented method of producing a diagnostic test sequence to diagnose a disease or disorder of a patient executed by a diagnostic tool is provided. The computer-implemented method includes arranging an order of a first plurality of diagnostic test procedures related to the disease or disorder identified for the patient, wherein arranging is based on a statistical probability information and time required to perform each of the first plurality of diagnostic test procedures, formatting a step of a first diagnostic test procedure from among the first plurality of diagnostic test procedures for display on a display device, displaying the formatted step on the display device, arranging an order of a second plurality of diagnostic test procedures, which includes one diagnostic test procedure of the first plurality of diagnostic test procedures, during execution of the first plurality of diagnostic test procedures, and based on intermediate diagnostic test information obtained from execution of the first plurality of diagnostic test procedures, and displaying a step of a second diagnostic test procedure from among the second plurality of diagnostic test procedures on the display device, wherein each of the above steps is performed by a computer.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 3 illustrates a representative test preparation step display image that can be prepared by the dynamic diagnostic test generator for display on a display device.

FIG. 4 illustrates a representative test step display image that can be prepared by the dynamic diagnostic test generator for display on a display device.

FIG. 7 illustrates an information display image that can be prepared by the dynamic diagnostic plan generator for display on a display device.

FIG. 8 illustrates a results display image that can be prepared by the dynamic diagnostic plan generator for display on a display device.

FIG. 14 illustrates a representative test preparation step display image that can be prepared by the dynamic diagnostic test generator for display on a display device according to an embodiment of the present disclosure.

FIG. 15 illustrates a representative test step display image that can be prepared by the dynamic diagnostic test generator for display on a display device according to an embodiment of the present disclosure.

DETAILED DESCRIPTION

Figure 1:
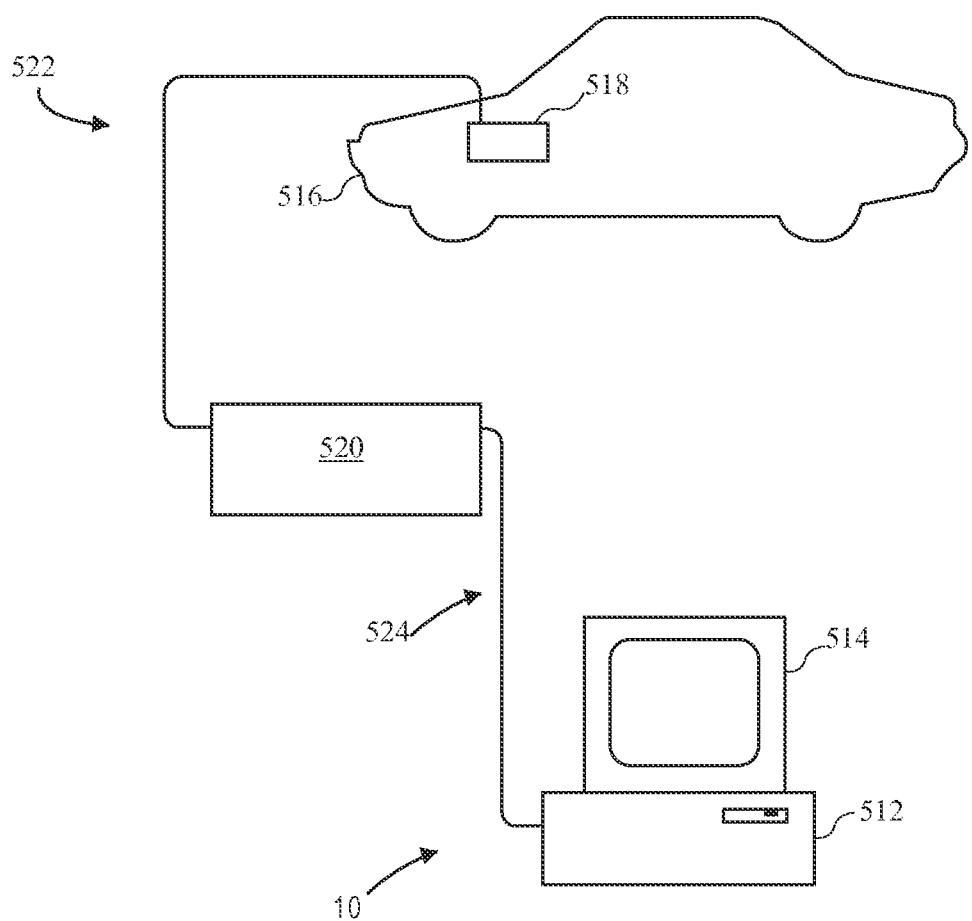
FIG. 1 illustrates an exemplary vehicle diagnostic test setup of a type suitable for carrying out the functions of an embodiment of the invention.

A diagnostic test sequence can navigate a vehicle technician through a step-by-step test sequence based on a vehicle onboard computer trouble code or codes, or a vehicle operational symptom or symptoms. During vehicle diagnostics, for example, test step instructions and information can be displayed to the vehicle technician on a display screen panel. Similarly, during a power tool diagnostic, test step instructions and information can be displayed to the power tool technician on the display screen panel. The power tool can include, drills, saws, impact drivers, compressors, grinder, sander, joiner, cutter, wrench, hammer, blower, rotary tools, pneumatic tools, measuring tools, fluid electronic timers, routers, oscillating tools, cleaner and the like.

The diagnostic test sequence can similarly navigate a medical technician or a doctor through a step-by-step test sequence based on a patient's symptoms. During diagnostic testing of a patient, for example, test step instructions and information can be displayed to the medical technician, such as a medical doctor on a display screen panel of a computing device, such as an IPad™ from Apple™.

A dynamic diagnostic plan generator can include a diagnostic test sequence optimizer that can arrange, or order, a sequence of diagnostic tests related to one or more symptoms to diagnose a failure mode of a vehicle, a power tool or a disease or disorder of a patient based at least in part on a failure mode or disease or disorder analysis. In addition, the sequence can be modified during test execution based on intermediate test results. The initial and iterative test sequence optimization, combined with the features below, can be referred to as "dynamic decision sequencing."

The diagnostic plan generator can also include a vehicle, a power tool or patient state tracker that can track the state of the vehicle/power tool/patient during and between diagnostic test procedures, and a test preparation step formatter that can format a test preparation step for display on a display device based at least in part on the vehicle/power tool/patient state. The diagnostic plan generator can further include a test procedure formatter that can format a sequence of test steps for display on a display device to provide instructions to a vehicle, power tool or medical technician for diagnosing the failure mode or disease or disorder. The diagnostic plan generator can also include an interactive diagnostic schematic generator that can illustrate a diagnostic test procedure, such as a wiring or anatomical diagram, for display on a display device.

In addition, the dynamic diagnostic plan generator can include an information object producer that can create a data structure including information related to the diagnostic test procedures. Furthermore, the diagnostic plan generator can include a failure mode or disease or disorder identifier sender that can send a failure mode or disease or disorder identifier over a communication network to a central database, a historical data receiver that can receive historical data regarding the outcomes of previous diagnostic testing, and a failure mode or disease or disorder analyzer updater that can update the failure mode or disease or disorder analysis based on the historical, data. Moreover, the diagnostic plan generator can include a failure mode or disease or disorder test authoring system that can be used by an expert vehicle, power tool or medical technician to create new failure mode or disease or disorder tests.

The invention will now be described with reference to the drawing figures, in which like reference numerals refer to like parts throughout. FIG. 1 illustrates a vehicle test configuration that is compatible with the present inventive method and apparatus. A dynamic diagnostic plan generator 10 can include a personal computer 512 with a display 514. In some embodiments, the dynamic diagnostic plan generator 10 can be coupled to a vehicle 516, including, for example, a vehicle onboard computer 518. For example, the dynamic diagnostic plan generator 10 can be coupled to the vehicle onboard computer 518 by way of a vehicle interface box 520, as shown in FIG. 1. The vehicle test configuration can further include electrical links 522, 524, such as wires, cables, data buses, a communication network or a wireless network. The dynamic diagnostic plan generator 10 can display diagnostic test procedure instructions to a vehicle or power tool technician to aid in performing vehicle or power tool diagnostics. The dynamic diagnostic plan generator 10 can also receive feedback from the vehicle 516 or the power tool (not shown).

Figure 2:
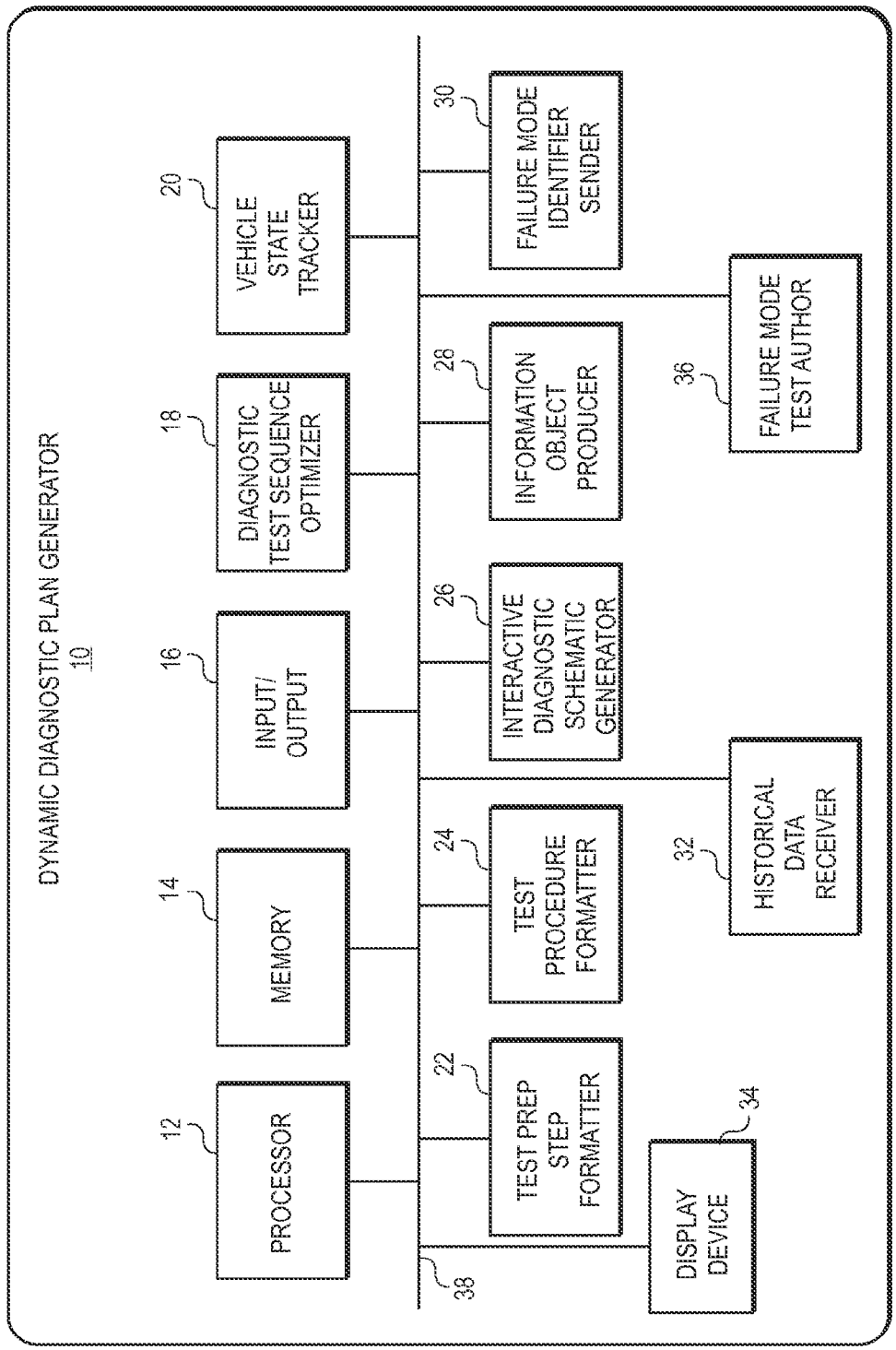
FIG. 2 is a schematic diagram illustrating a dynamic diagnostic plan generator according to a preferred embodiment of the invention.

An embodiment of the present inventive method and apparatus can generate a dynamic diagnostic plan to diagnose a failure mode of a vehicle, power tool or a disease or disorder of a patient based on one or more symptoms. FIG. 2 illustrates a dynamic diagnostic plan generator 10 for use with, for example, a PC-based vehicle, power tool or patient diagnostic system to provide instructions for expert diagnostic procedures to allow a vehicle, power tool or a medical technician to identify the cause of a trouble code or fault or vehicle operational problem or a symptom at the component level. A related diagnostic method for use with a vehicle diagnostic system of this type is disclosed in U.S. Pat. No. 5,631,831, entitled "Diagnosis Method for Vehicle Systems," to Bird, et al. dated May 20, 1997, the disclosure of which is hereby incorporated by reference in its entirety.

The dynamic diagnostic plan generator 10 can include a processor 12, a memory 14, an input/output device 16, a diagnostic test sequence optimizer 18, a vehicle, power tool or patient state tracker 20, a test preparation step formatter 22, a test procedure formatter 24, an interactive diagnostic schematic generator 26, an information object producer 28, a failure mode or disease or disorder identifier sender 30, a historical data receiver 32, a display device 34, and a failure mode or disease or disorder test author 36, all of which can be interconnected by a data link 38. The processor 12, the memory 14, the input/output device 16 and the display device 34 can be part of a general computer, such as a personal computer (PC), a notebook, tablet, a UNIX workstation, a server, a mainframe computer, a personal digital assistant (PDA), wearable mounted device, or some combination of these. Alternatively, the processor 12, the memory 14 and the input/output device 16 can be part of a specialized computing device, such as a vehicle diagnostic scan tool or a medical device such as a magnetic resonance imaging (MRI). The remaining components can include programming code, such as source code, object code or executable code, stored on a computer-readable medium that can be loaded into the memory 14 and processed by the processor 12 in order to perform the desired functions of the dynamic diagnostic plan generator 10.

In various embodiments, the dynamic diagnostic plan generator 10 can be coupled to a communication network, which can include any viable combination of devices and systems capable of linking computer-based systems, such as the Internet; an intranet or extranet; a local area network (LAN); a wide area network (WAN); near-field communication (NFC), a direct cable connection; a private network; a public network; an Ethernet-based system; a token ring; a value-added network; a telephony-based system, including, for example, T1 or E1 devices; an Asynchronous Transfer Mode (ATM) network; a wired system; a wireless system; an optical system; a combination of any number of distributed processing networks or systems or the like.

An embodiment of the dynamic diagnostic plan generator 10 can be coupled to the communication network by way of the local data link, which in various embodiments can incorporate any combination of devices—as well as any associated software or firmware—configured to couple processor-based systems, such as modems, network interface cards, serial buses, parallel buses, LAN or WAN interfaces, wireless or optical interfaces and the like, along with any associated transmission protocols, as may be desired or required by the design.

Additionally, an embodiment of the dynamic diagnostic plan generator 10 can communicate information to the user and request user input by way of an interactive, menu-driven, visual display-based user interface, or graphical user interface (GUI). The user interface can be executed, for example, on a personal computer (PC) with a mouse and keyboard, with which the user may interactively input information using direct manipulation of the GUI. Direct manipulation can include the use of a pointing device, such as a mouse or a stylus, to select from a variety of selectable fields, including selectable menus, drop-down menus, tabs, buttons, bullets, checkboxes, text boxes, and the like. Nevertheless, various embodiments of the invention may incorporate any number of additional functional user interface schemes in place of this interface scheme, with or without the use of a mouse or buttons or keys, including for example, a trackball, a touch screen or a voice-activated system.

The diagnostic test sequence optimizer 18 can select and arrange in order a group of diagnostic test procedures that are related to a symptom of a patient, a power tool, a vehicle operational problem or an onboard computer trouble code. An example of a diagnostic test sequence optimizer 18 that is compatible with the dynamic diagnostic plan generator 10 is disclosed in a copending U.S. patent application, entitled "Diagnostic Test Sequence Optimization Method and Apparatus," filed concurrently herewith by Fountain, et al., the disclosure of which is hereby incorporated by reference in its entirety.

The diagnostic test procedure sequence can be based, for example, on a diagnostic Failure Mode and Effects Analysis (FMEA) or on an author priority setting. A FMEA, or equivalently, a Failure Mode and Effects Criticality Analysis (FMECA), is a widely used tool in manufacturing industries, for example, the aerospace industry, the automotive industry, the heavy equipment industry and the digital electronics industry. FMEA has also been used in the health and power tool industries.

A typical FMEA can include a list of failure modes or disease or disorder, causes and effects associated with each of the failure modes or diseases or disorders, a severity of each failure mode or disease or disorder, a risk or probability of the occurrence of each failure mode or disease or disorder, and additional information that can be useful in designing and manufacturing the associated product or component. FMEA can also be used to predict the likelihood of a disease or disorder of a patient's organs, such as a heart, due to the symptoms being assessed including increase blood pressure or cholesterol levels. For example, the FMEA can include estimated probability information based on engineering analysis or statistical probability estimates based on empirical data from actual failures. Thus, each diagnostic test procedure can be an individual failure mode or disease or disorder test based on the failure modes or disease or disorder identified in the FMEA, and the FMEA information can be used to determine which of the diagnostic test procedures is most likely to identify the cause of the symptom.

In addition, the diagnostic test procedure sequence can be based on multiple symptoms. For example, the diagnostic test sequence optimizer 18 can evaluate two or more simultaneously occurring or intermittent symptoms in order to identify a possible common cause. Furthermore, the diagnostic test sequence optimizer 18 can dynamically reorder the test procedure sequence during test execution based on an interrelation of two or more symptoms. For example, the diagnostic test sequence optimizer 18 may identify a common voltage source for two sensors that simultaneously have symptoms, and reorder the test sequence to verify the functionality of the common voltage source before performing failure mode or disease or disorder tests on the individual sensors, such as a heart or brain sensor. Once again, the test sequence can also be based on the comparative failure rates of the individual sensors and the common voltage source.

In another embodiment, if the symptoms include increased blood pressure, which may be caused by a plaque build-up in the blood vessels, the heart or the kidney may not be functioning properly, the diagnostic test sequence optimizer 18 can dynamically reorder the test sequence to conduct a body scan of the heart, blood vessels and kidney before performing the individual tests on these components.

Moreover, in some embodiments of the dynamic diagnostic plan generator 10, the diagnostic test sequence optimizer 18 can dynamically reorder the test sequence during test execution based on intermediate results, for example, based on the results of a particular failure mode or disease or disorder test or a combination of failure mode or disease or disorder tests. For example, even though a particular failure mode or disease or disorder test does not result in a final diagnosis, the failure mode or disease or disorder test, alone or in combination with one or more other failure mode or disease or disorder tests, can validate the correct functionality of a component. As a result, the diagnostic test sequence optimizer 18 can dynamically reorder the test sequence, for example, to omit further failure mode or disease or disorder tests corresponding the validated component, or to move remaining failure mode or disease or disorder tests corresponding the validated component to a later position of lesser priority in the test sequence.

Similarly, in some embodiments of the dynamic diagnostic plan generator 10, the diagnostic test sequence optimizer 18 can dynamically reorder the test sequence during diagnostic test execution based on new information derived from a particular failure mode or disease or disorder test, although the failure mode or disease or disorder test does not result in a final diagnosis. For example, the discovery of an additional symptom during a particular failure mode or disease or disorder test can result in the diagnostic test sequence optimizer 18 modifying the test sequence based on the interrelation of the newly discovered symptom and the previously known symptom or symptoms. Thus, the diagnostic test sequence optimizer 18 can perform iterative, dynamic, run-time reevaluations during diagnostic test execution to continually modify or recreate the test sequence.

Some existing diagnostic test systems include sequences of diagnostic test procedures that can performed on a patient, a vehicle or other product, such as power tool to determine a cause of a symptom. However, in some existing systems the sequence of the diagnostic tests is determined based solely on the priority assigned by an expert diagnostic author.

An embodiment of the present invention can have the advantage that the diagnostic test procedure sequence can be optimized using statistical probability information based on historical outcomes of actual diagnostic testing in order to more accurately determine the efficacy of each of the diagnostic procedures. As a result, the diagnostic test procedure sequence can be customized to minimize or optimize the time required to resolve the problem, the cost required to resolve the problem, additional factors that can affect the problem resolution, a combination of these factors, or the like.

The diagnostic test sequence optimizer 18 can perform an analysis of the comparative utility of each of the individual diagnostic procedures based on various factors that can affect problem resolution. For example, the failure mode or disease or disorder analysis factors can include, but are not limited to, any of the following:

an estimated time required to perform a diagnostic test the difficulty of performing the diagnostic test an estimated time required to remove and replace a component (heart with an artificial heart) associated with the diagnostic test the difficulty of removing and replacing the component the level of expertise of a vehicle or power tool service technician or medical technician (including medical doctors) performing the diagnostic procedure the availability of a replacement component (including organ transplants, skin grafts, implants, prosthetics, and the like)

the estimated cost or the actual cost of the component the estimated or actual cost of labor empirical data regarding the probability that a failure mode or disease or disorder associated with the individual diagnostic procedure exists given the existence of a specified symptom (e.g., FMEA data)

an estimate of the probability that the failure mode or disease or disorder exists given the existence of the symptom a frequency or rate of the failure mode or disease or disorder associated with the diagnostic procedure the mileage of the subject vehicle the number of rotation of saw blade breaking condition of the power tool
usage cycle of the power tool
the year of the subject vehicle
age of the patient
age of the power tool
safety alerts of the replacement medical component
safety alerts of the replacement power tool component such as drill bit, saw blade, and so forth
previous surgery on that component (previous heart surgery)
time between other surgery
other existing medical conditions
availability of other medical technicians, such as an radiologist or anesthesiologist
the specific configuration of the vehicle or the power tool or a modification that has been performed on the vehicle or the power tool
the vehicle or the power tool maintenance record
the patient's medical history
a service center maintenance record regarding the vehicle or the power tool or associated vehicles or the power tools
a manufacturer warranty record associated with the specific vehicle or the power tool or a type of vehicle or the power tool
a manufacturer warranty record associated with the specific component
a recommended maintenance schedule, such as a manufacturer recommended maintenance schedule, or
a technical service bulletin issued by the vehicle manufacturer.

In addition, the diagnostic test sequence optimizer 18 can assign a weight, or weighting, to each of the factors used in the failure mode or disease or disorder analysis. For example, a heavier weighting can be given to the time required to perform an individual diagnostic procedure versus the cost of performing the procedure and replacing an associated component. Conversely, the cost can be weighted heavier than the time required. Similarly, a greater weight can be assigned to the difficulty of performing the diagnostic procedure, for example, in relation to the expertise level of the vehicle, the power tool or medical technician. Greater weight may be on the availability of another medical technician such as a surgeon or a radiologist or an anesthesiologist.

In other cases, a greater weighting may be placed on the availability of a replacement component, including where the patient is in line for an organ transplant or whether a limb that fits the patient is available. For example, a diagnostic procedure related to a component that is not available may be given a particularly low weighting. In yet other cases, a heavier weighting can be assigned to a diagnostic procedure associated with a recommended maintenance procedure that is coming due, for example, based on the vehicle mileage or age of the power tool, and has not been performed on the subject vehicle or the power tool. In the medical field, the recommended maintenance procedure may be a mammogram for women over 40 years old. Similarly, a heavy weighting can be placed on a diagnostic procedure related to a technical service bulletin, such as a recommended technical service bulletin issued by the vehicle or the power tool manufacturer. Further, a heavy weighting can be placed on a diagnostic procedure related to a bulletin, such as a recommended technical service bulletin issued by the vehicle or the power tool manufacturer or guidelines by National Institutes of Health.

Furthermore, the weights can be partially determined based on user preferences. For example, a user preference setting can be set by a diagnostic procedure author, by a service or medical center, by a vehicle, the power tool or medical technician, or by a combination thereof, and subsequently factored into the individual weightings of the factors. For example, a service or medical center or a vehicle, the power tool or medical technician may prefer to minimize either time or cost, depending on the vehicle or the power tool type, urgency of medical attention needed, customer feedback or the like. Thus, a user input can be used by the diagnostic test sequence optimizer 18 in determining the weightings of certain critical factors in accordance with user preferences.

Moreover, the diagnostic test sequence optimizer 18 can receive a history of the vehicle or the power tool, for example, a maintenance or repair record kept with the vehicle or the power tool, at a service center, or by the manufacturer. For example, the vehicle or power tool history can include information such as the mileage on the subject vehicle or age of the power tool, the specific configuration of the vehicle, a modification such as a technical service bulletin that has been performed on the vehicle or power tool, a vehicle or power tool maintenance record, a service center maintenance record associated with the specific vehicle or power tool or type of vehicle or power tool, or a manufacturer warranty record associated with the specific vehicle or power tool or type of vehicle or power tool or component having problems.

Similarly, the diagnostic test sequence optimizer 18 can receive a medical history of the patient, for example, a medical record at the medical center. For example, the medical history can include information such as the age of the patient, previously diagnosed diseases, immunizations, current and past prescribed drugs, weight, height, family medical history or predispositions and the like.

Accordingly, the diagnostic test sequence optimizer 18 can use the results of the failure mode or disease or disorder analysis, the vehicle or power tool history or patient medical history, user settings received by way of user input, a diagnostic FMEA or other input factors to order the diagnostic test procedures in a sequence. The sequence can be optimized in accordance with, for example, a priority input by a diagnostic test procedure author, a user preference input and any combination of the failure mode or disease or disorder analysis factors. Thus, the diagnostic test sequence optimizer 18 is highly and dynamically configurable to allow customization of the sequence optimization process.

In addition, the vehicle or power tool state tracker 20 can track the state of the vehicle or power tool during and between individual diagnostic test procedures. The vehicle or power tool state tracker 20 can help to eliminate duplication of efforts during a diagnostic test sequence by keeping track of the current vehicle or power tool test configuration and providing test preparation steps to reconfigure the vehicle or power tool between individual diagnostic procedures without redundant steps. The vehicle or power tool state tracker 20 can track the current state of the vehicle or power tool by maintaining a current list of preconditions, or vehicle or power tool test configuration information.

In addition, the patient state tracker 20 can track the state of the patient during and between individual diagnostic test procedures. The patient state tracker can help to eliminate duplication of efforts during a diagnostic test sequence by keeping track of the current testing and equipment being used, and providing test preparation steps to reconfigure the room or equipment being used or the patient (e.g. administering pain medication) between individual diagnostic procedures without redundant steps. The patient state tracker can track the current state of the patient by maintaining a current list of preconditions, or patient test information.

An example of a method for tracking the vehicle state for use with a vehicle diagnostic system is disclosed in a copending U.S. patent application, entitled "Vehicle State Tracking Method and Apparatus for Diagnostic Testing," filed concurrently herewith by Fountain, et al., the disclosure of which is incorporated by reference in its entirety.

The vehicle/power tool/patient state tracker 20 can determine a set of preconditions, or vehicle/power tool/patient test configuration requirements, necessary for an individual diagnostic test procedure. Preconditions and corresponding test preparation steps can be created, or authored, for example, by an expert diagnostics technician. Preconditions can also be formatted to be reusable in various diagnostic test procedures, which can save time during the authoring phase of diagnostic test procedures.

In operation, the vehicle/power tool/patient state tracker 20 typically can determine the preconditions required for a subsequent diagnostic test procedure before the completion of a current diagnostic test procedure in order to prevent or minimize redundant efforts at the completion of the current diagnostic procedure and at the initiation of the subsequent diagnostic procedure. The vehicle/power tool/patient state tracker 20 can read the current state of the vehicle/power tool/patient, for example, from a memory register. In some embodiments, the vehicle/power tool/patient state can be stored in a processor register, while in other embodiments the vehicle/power tool/patient state can be stored in a main memory register or in a memory register of a storage device associated with the dynamic diagnostic plan generator 10.

The vehicle/power tool/patient state tracker 20 can verify a current setting of the vehicle/power tool/patient state with regard to a specific precondition, or a group of current settings corresponding to a number of preconditions. If a precondition is required for the subsequent test procedure and the corresponding vehicle/power tool/patient state setting is currently not valid, the test preparation step formatter 22 can format a test preparation step for display on the display device 34 to instruct the vehicle, power tool or medical technician to set up the required precondition or vehicle/power tool/patient test configuration. As an example, FIG. 3 illustrates a representative test preparation step display screen 40 that can be prepared by the test preparation step formatter 22. Similarly, FIG. 14 illustrates a representative medical test preparation step display screen 40. Of course, if the precondition is required for the subsequent test procedure and the corresponding vehicle/power tool/patient state setting is currently valid, the test preparation step formatter 22 may elect not to format a test preparation step for display.

In addition, the vehicle/power tool/patient state tracker 20 can receive feedback indicating when the precondition has been satisfied. For example, the vehicle/power tool/patient state tracker 20 can receive a data signal from the vehicle onboard computer indicating that the precondition has been satisfied. In some embodiments, the vehicle/power tool/patient state tracker 20 can receive a feedback signal from test equipment, such as a digital multimeter coupled to the vehicle or power tool or a blood pressure monitor coupled to the patient. Similarly, the vehicle/power tool/patient state tracker 20 can receive user input from the vehicle, power tool or medical technician by way of the input/output device 16 indicating that the precondition has been satisfied, or that the vehicle, power tool or patient technician has complied with the test preparation step instructions.

Once the precondition has been satisfied, the vehicle/power tool/patient state tracker 20 can update the vehicle/power tool/patient state, for example, in a memory register, to reflect a valid setting corresponding to the precondition. Thus, the vehicle/power tool/patient state can be continually and dynamically updated to maintain a current and accurate vehicle/power tool/patient state that is available to the diagnostic system at any time in order to determine test preparation steps required to reconfigure the vehicle/power tool/patient between diagnostic procedures in a diagnostic test sequence.

In the case that the vehicle/power tool/patient condition is currently valid but is not required for a subsequent test procedure, the test preparation step formatter 22 can format a test preparation step for display instructing the vehicle, power tool or medical technician to reverse, or undo, the vehicle/power tool/patient condition. Correspondingly, the vehicle/power tool/patient state tracker 20 can receive feedback as described above and herein indicating that the condition has been reversed, and can update the vehicle/power tool/patient state, for example, in a memory register, to reflect an invalid setting corresponding to the condition, or precondition.

The vehicle/power tool/patient state tracker 20 can maintain vehicle/power tool/patient state settings for any number of vehicle/power tool/patient preconditions associated with the diagnostic test procedures which can be configured to be readily available for use, or reuse, with any existing test procedure or with a new test procedure. For example, preconditions can include, but are not limited to, any of the following:

blood pressure level
heart rate
pain level
heart rate monitor
IV line
preparation of surgical area on the patient
an ignition switch position
a light switch position
an engine run condition
a throttle position
sensing system position
detection system connection condition
kick-back system connection condition
a braking system condition
an engine speed
drill bit rotation speed
saw blade rotation speed
a vehicle speed
a test equipment connection
a vehicle or power tool electrical connection condition
an ambient air temperature
an engine inlet temperature
an engine lubricant pressure
engine lubricant temperature
an engine lubricant level
an engine coolant temperature
an engine coolant specific gravity
an engine exhaust gas temperature
an engine exhaust gas content
a transmission setting
a brake pedal position
a parking brake position
a brake fluid pressure
a fuel level
a fuel supply pressure
a battery voltage
a battery charging system voltage
a battery charging system current
an ignition voltage
an ignition current
an engine cylinder compression
a vehicle or power tool configuration, or
a vehicle or power tool modification.

Figure 5:
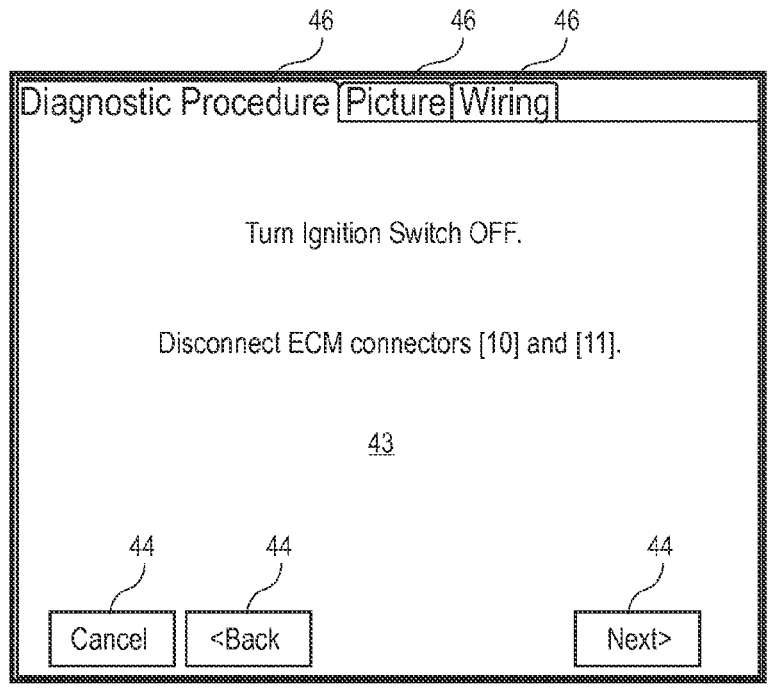
FIG. 5 illustrates a representative instruction display image that can be prepared by the dynamic diagnostic plan generator for display on a display device.

In addition, the dynamic diagnostic plan generator 10 can include a test procedure formatter 24 that can prepare the sequence of diagnostic test procedures for display on the display device. As an example, FIG. 4 illustrates a representative procedure display screen 42 that can be prepared by the test procedure formatter 24. FIG. 15 also illustrates a representative procedure display that can be prepared by the test procedure formatter 24. The test procedure formatter 24 can also prepare more detailed test preparation steps for display, for example, as shown in the detailed test procedure display screen 43 illustrated in FIG. 5. The test procedure formatter 24 can further format navigational buttons 44, such as the "Cancel," "Back" and "Next" buttons shown in FIG. 5, as well as additional navigational aids, such as the tabs 46 shown in FIG. 5.

An embodiment of the present invention communicates information to the user and requests user input by way of an interactive, menu-driven, visual display-based user interface. The dynamic diagnostic plan generator 10 can include input/output devices 16, such as a mouse and keyboard, with which the user may interactively input information using direct manipulation of a graphical user interface (GUI). Direct manipulation includes using a pointing device, such as a mouse, to select from a variety of selectable fields, including selectable menus, tabs, buttons, bullets, checkboxes, text boxes, and the like. Nevertheless, other embodiments of the invention may incorporate any number of additional functional user interface schemes in place of this interface scheme, with or without the use of a mouse or buttons or keys, including for example, a trackball, a touchscreen or a voice-activated system.

Figure 6:
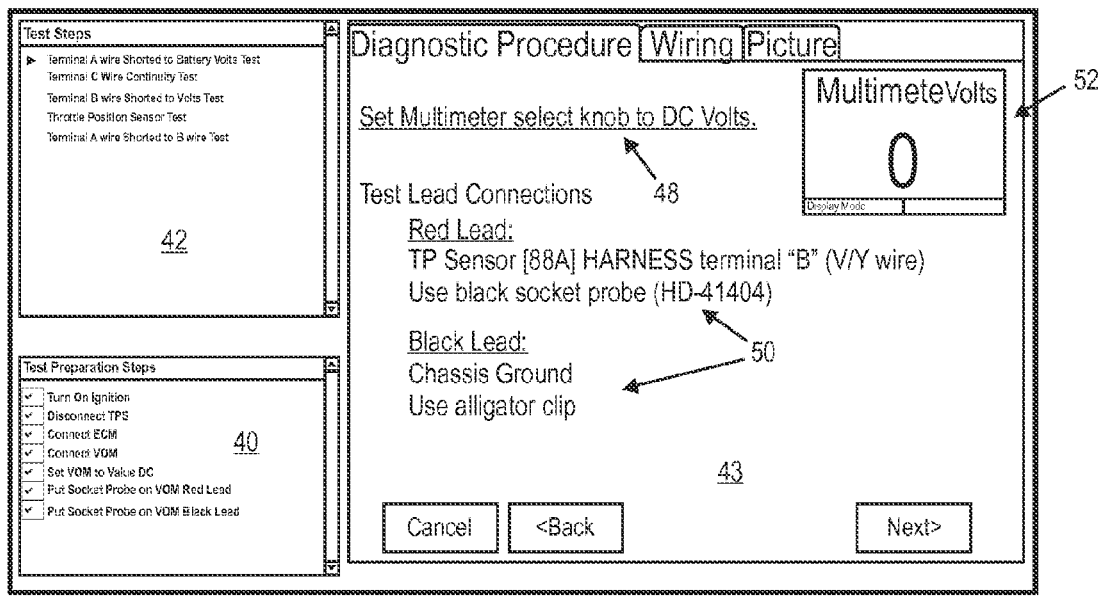
FIG. 6 illustrates a representative diagnostic procedure display image that can be prepared by the dynamic diagnostic plan generator for a display on a display device.

Similarly, the test procedure formatter 24 can prepare detailed test step instructions, as shown in display image 43, such as the representative test instruction 48, "Set Multimeter select knob to DC Volts," shown in FIG. 6. The test procedure formatter 24 can also provide detailed test setup instructions, for example, the representative test lead connections instructions 50. In addition, the test procedure formatter 24 can prepare test equipment display images, such as the multimeter display 52 shown in FIG. 6. In some embodiments, the dynamic diagnostic plan generator 10 can further receive dynamic input data, for example, a digital multimeter or blood pressure monitor input for real-time display. The step instructions may also be formatted for use with power tools.

Furthermore, the test procedure formatter 24 and the test preparation step formatter 22 can cooperate to prepare combined display windows 50, such as the test step display image 42, the test preparation step display image 40 and the diagnostic procedure display image 43 shown in FIG. 6, which can be displayed simultaneously on the display device 34.

Moreover, the test procedure formatter 24 can prepare additional informational display images, such as a "description" display image (not shown) or an "information" display image 56, as shown in FIG. 7. Similarly, the test procedure formatter 24 can prepare a "results" display image 58 as shown in FIG. 8. In addition, the test procedure formatter 24 can provide specific instructions for reconfiguring the vehicle/power tool/patient after a test procedure or a diagnostic test sequence has been completed, such as the reconfiguration instructions 60 shown in FIG. 8. Optionally, an embodiment of the diagnostic plan generator 10 can provide the vehicle, power tool or medical technician with the option of storing the results of a diagnostic procedure in a memory 14, for example, with a "Log Test" button 62.

Figure 9:
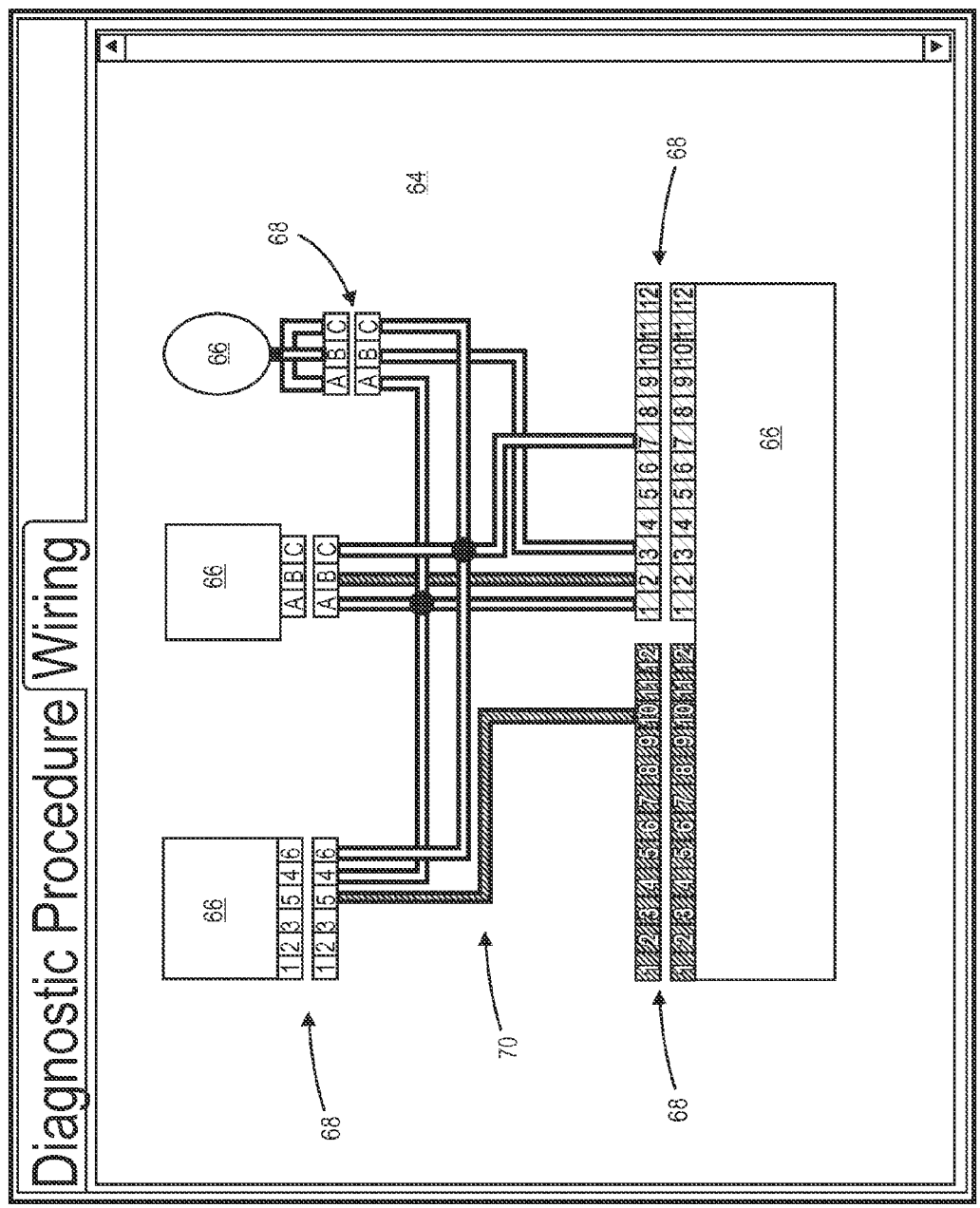
FIG. 9 illustrates a wiring schematic display image that can be prepared by the dynamic diagnostic plan generator for display on a display device.

The interactive diagnostic schematic generator 26 can generate a diagnostic schematic, such as the representative diagnostic schematic 64 illustrated in FIG. 9. An example of an interactive diagnostic schematic generator 26 that is compatible with the dynamic diagnostic plan generator 10 is disclosed in a copending U.S. patent application, entitled "Interactive Schematic Generating Method and Apparatus for a Vehicle Diagnostic Procedure," filed concurrently herewith by Fountain, et al., the disclosure of which is hereby incorporated by reference in its entirety.

The interactive diagnostic schematic 64 can illustrate any number of vehicle components 66 or patient or power tool components (not shown). For example, the vehicle components 66 in FIG. 9 could represent a bank angle sensor, a throttle position sensor, a cam position sensor and an electronic control module, or any additional vehicle components 66 related to a diagnostic procedure. Examples of patient components may include the heart, brain, kidneys and the like while examples of power tool components may include power buttons, drill speed switch, motor windings, batteries and the like.

In order to generate the interactive diagnostic schematic 64, the interactive diagnostic schematic generator 26 can read a schematic data file associated with a diagnostic test procedure, for example, a wiring or anatomical diagram data file. For example, the interactive diagnostic schematic generator 26 can read a data file from a main memory or from a peripheral memory device associated with the processor 12. In a preferred embodiment of the invention, the schematic data file can be stored in a scalable vector graphics (SVG) file format, which is an XML-based markup language for describing two-dimensional vector graphics, both static and animated (i.e., either declarative or scripted). Thus, the schematic data file can be stored as a text file.

SVG formatting can allow various types of graphic objects, for example, vector graphic shapes consisting of straight lines and curves and the areas bounded by them, raster graphics images or text. SVG formatting further can allow graphical objects to be grouped, styled, transformed and composited into previously rendered objects. SVG formatting can also permit nested transformations, clipping paths, alpha masks, filter effects, template objects and extensibility. In addition, SVG formatting can enhance searchability and accessibility of the graphics.

The interactive diagnostic schematic 64 can be dynamic and interactive. For example, a document object model (DOM) in SVG formatting can allow straightforward and efficient animation of graphics by way of script languages. The SVG graphics file format is also compatible with popular communications network standards, such as World Wide Web standards on the Internet. Additionally, SVG images can be stored using compression techniques.

SVG data files can be prepared for display on a display device 34 by any number of commercially available SVG viewers, such as the Adobe SVG Viewer, produced by Adobe Systems Incorporated of San Jose, Calif., or the Corel SVG Viewer, produced by the Corel Corporation of Ottawa, Canada.

The interactive diagnostic schematic generator 26 can modify the schematic data file to indicate a test subject in the schematic. For example, the interactive diagnostic schematic generator 26 can alter the color of the vehicle component 66, electrical connector 68, wire 70, or the like, and can highlight the test subject by surrounding the test subject with a highlighting color to make the test subject stand out from the background and the remaining items in the schematic. This can also be done with patient components such as brain, heart, kidney and the like or power tool components such as power buttons, drill speed switch, motor windings, batteries and the like.

Likewise, the interactive diagnostic schematic generator 26 can shade the test subject, fade the color of the test subject, gray out the test subject, or animate the test subject. For example, the interactive diagnostic schematic generator 26 can animate the test subject by making the vehicle component 66, electrical connector 68, wire 70, or the like, blink or flash in the schematic 64 when displayed on a display device 34. This can be accomplished, for example, by adding executable code in a scripting language to the schematic data file. This can also be done with patient components such as brain, heart, kidney and the like or power tool components such as power buttons, drill speed switch, motor windings, batteries and the like.

Similarly, the interactive diagnostic schematic generator 26 can animate the test subject by adding motion to the schematic 64, for example, demonstrating the connection or disconnection of an electrical connector 68 or a neural connection between neurons in the brain. The interactive diagnostic schematic generator 26 can also zoom in on a specific component 66, for example, when a user clicks on the component 66 using a pointing device, such as a mouse or use fingers motions on the touch screen display. Furthermore, the interactive diagnostic schematic generator 26 can add properties to the component 66, for example, a part number, inventory information regarding the component, a link to a help file, or the like.

The interactive diagnostic schematic generator 26 can illustrate a location on the schematic 64 where a test equipment connection is required. For example, the interactive diagnostic schematic generator 26 can highlight or otherwise locate a location or multiple locations where electrical connectors, pins, clamps, or the like associated with test equipment are to be connected to the vehicle component 66 or electrical connector 68. The interactive diagnostic schematic generator 26 can further illustrate required test equipment, such as a digital multimeter, in the schematic 64. Similarly, the test equipment locations where pads for an EKG machine needs to be located to measure the heart can be highlighted and illustrate the required test equipment, such an EKG machine. For power tools, the test lead locations to test battery connections on a drill can be highlighted and illustrate the required test component, such as a volt meter. This can aid a vehicle, power tool or medical technician to quickly and efficiently connect test equipment for a diagnostic test procedure.

The diagnostic schematic generator 26 can format the originally stored schematic or a modified schematic for display on the display device 34. For example, the diagnostic schematic generator 26 can include an SVG viewer or cooperate with an SVG viewer to display the diagnostic schematic generator 26.

The interactive diagnostic schematic generator 26 can receive feedback, for example, by direct manipulation such as a user selecting a portion of the schematic using a mouse, finger or the equivalent. For example, a user can "click" on a wire, a component, or another test subject within a schematic currently displayed on the screen, and the feedback receiver 36 can uniquely identify the selected test subject.

In response to the feedback, the interactive diagnostic schematic generator 26 can, for example, remove or discontinue the indication of the test subject in the schematic. That is to say, the test subject indicator 30 can remove or discontinue the highlighting, fading, graying out or animation of the test subject in the diagnostic schematic 10. Furthermore, in some embodiments, online help can be accessed by way of direct manipulation of displayed objects in the schematic.

In addition, in response to the feedback, the interactive diagnostic schematic generator 26 can mark the test subject to indicate that a diagnostic procedure, test step or other action has been performed on the test subject. Once again, the schematic generator 26 can use highlighting, shading, fading, graying out or animation of the test subject to indicate that the action has been performed. For example, the marking style used to mark the test subject to indicate that the action has been performed can be visually distinct from the indicating style used to indicate the test subject on which an action is required.

The information object producer 28 can create a diagnostic data structure, or information object, based on information related to the diagnostic test procedures. For example, the information object can include the diagnostic test procedure instructions, a list of possible causes of the symptom, the vehicle history, the power tool history, the patient history, the current state of the vehicle/power tool/patient, a diagnostic schematic, a Failure Mode and Effects Analysis (FMEA) compiled by the vehicle manufacturer or a component manufacturer, or the like.

Thus, the information object can include, but is not limited to, information such as the following:
- an estimated time required to perform the diagnostic test procedures
- a difficulty level of performing the diagnostic test procedures an estimated time required to remove and replace a component associated with the diagnostic test procedures
- a difficulty level of removing and replacing a component
- availability of other technicians such as a radiologist
- an availability of a replacement component
- wait time until a donor is available
- an estimated cost of the component
- an actual cost of the component
- an estimated cost of performing the diagnostic test procedures
- empirical data regarding the probability that a failure mode or disease or disorder exists given the existence of the symptom
- an estimate of the probability that a failure mode or disease or disorder exists given the existence of the symptom
- a frequency or rate of the failure mode or disease or disorder
- a vehicle mileage
- age of the patient or power tool
- a vehicle or power tool configuration
- a vehicle or power tool modification
- previous surgery or amputation
- a vehicle or power tool maintenance record
- a service center maintenance record
- medical center medical records
- a manufacturer warranty record
- the recommended maintenance schedule for the vehicle, or power tool, or
- a technical service bulletin.

The failure mode or disease or disorder identifier sender 30 can send a failure mode or disease or disorder identifier (I.D.) indicating the failure mode or disease or disorder over a communication network to a central database. For example, the failure mode or disease or disorder identifier can be sent to a service or medical center database, a manufacturer warranty database, or the like, over the Internet, an intranet, or a wireless network. In addition, the failure mode or disease or disorder identifier can include additional information associated with the diagnostic case, such as observed symptoms, diagnostic trouble codes (DTCs), a vehicle identification, a vehicle or power tool history, age of the patient, a vehicle/power tool/patient state as measured and observed, systematic data readings, specific parameters relevant to the optimization process (for example, any of the factors enumerated above), and the final diagnostic conclusion. The final diagnostic conclusion, can include a failure-mode identifier or a no-failure-mode-identified diagnosis. In this manner, the failure mode or disease or disorder occurrences can automatically be gathered in a central database in order to allow analysis of failure mode or disease or disorder occurrences to continually or dynamically update the statistical failure mode or disease or disorder information.

The historical data receiver 32 can receive failure mode or disease or disorder historical data over a communication network from a central database, for example, the results of a Failure Mode and Effects Analysis performed by the vehicle or power tool manufacturer using automatically-updated information from a region, a country, or an entire fleet of vehicles, line of power tools or from a prosthetic limb manufacturer. The historical failure mode or disease or disorder data can be used by the diagnostic test sequence optimizer 18 to order the diagnostic test procedures in an optimal sequence based on the latest updated information available. As a result, the diagnostic test sequence compiled by the dynamic diagnostic plan generator 10 can change over time in a dynamic manner, based on actual failure mode or disease or disorder occurrences.

Furthermore, the failure mode or disease or disorder test author 36 can provide a vehicle/power tool/patient diagnostic system authoring capability to facilitate the creation of failure mode or disease or disorder test procedures by an individual who is an expert in vehicle/power tool/patient diagnostics but is not necessarily knowledgeable concerning a computer programming language. The failure mode or disease or disorder test author 36 can accelerate development and reduce errors in diagnostic software by eliminating the need for a computer programmer to code the process as explained by an expert in vehicle diagnostics. Thus, the failure mode or disease or disorder test author 36 can be particularly useful to an original equipment manufacturer for developing electronic diagnostic sequences.

A related method for authoring diagnostic procedures for use with a vehicle diagnostic system is disclosed in U.S. patent application Ser. No. 11/052,118, entitled "Authoring Diagnostic Test Sequences Apparatus And Method," filed by Fountain, et al., on Feb. 8, 2005, the disclosure of which is hereby incorporated by reference in its entirety.

Figure 10:
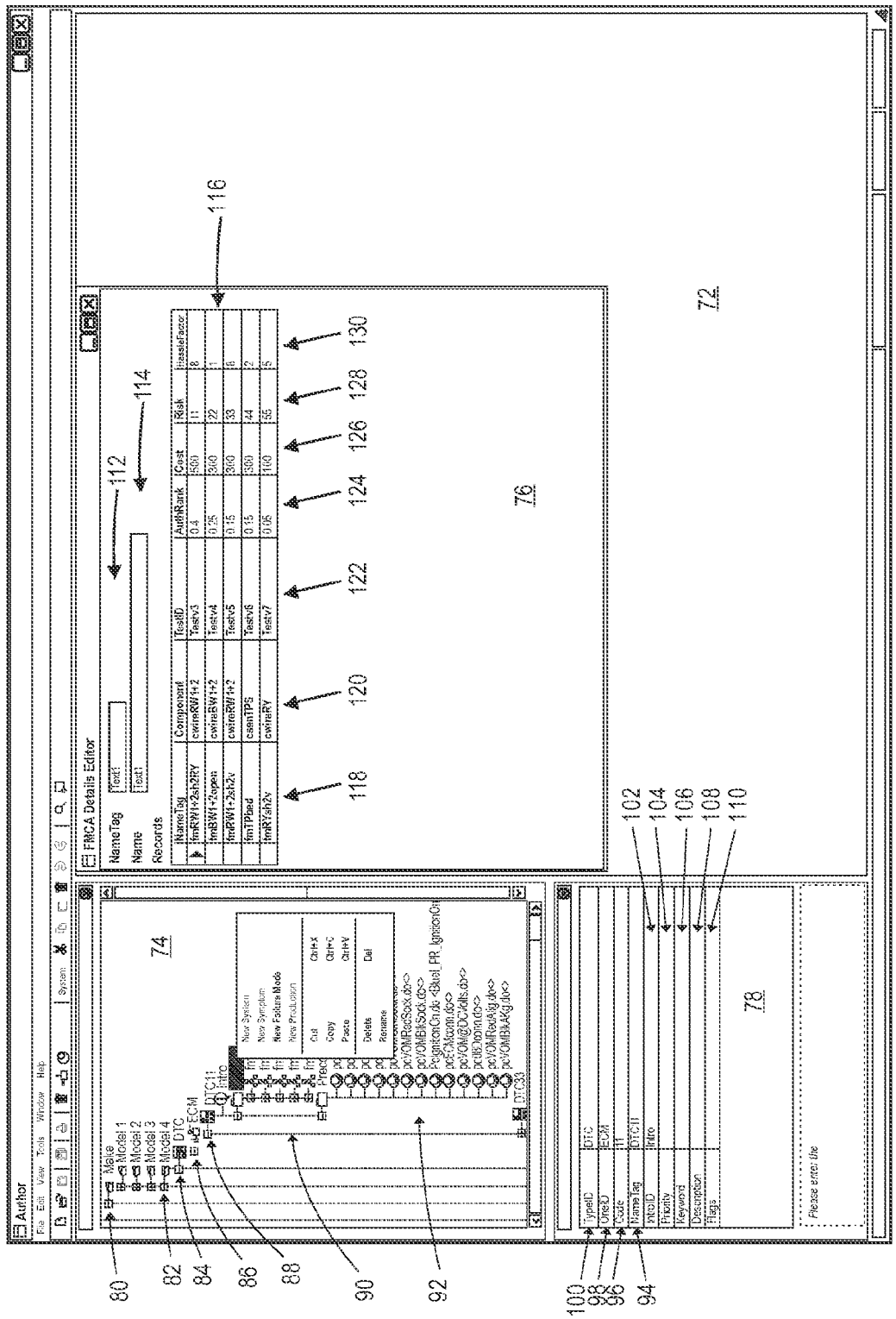
FIG. 10 illustrates an author display image that can be prepared by the dynamic diagnostic plan generator for display on a display device.

A representative failure mode or disease or disorder authoring display image is shown in FIG. 10, comprising a graphical user interface (GUI) work environment for use by an expert author to develop a test structure for a failure mode or disease or disorder test. The work environment can include a test structure display image 74, a FMEA details editor display image 76 and a symptom properties display image 78. The failure mode or disease or disorder test work environment can allow a diagnostics author to interactively create a failure mode or disease or disorder test that can be used in a diagnostic test sequence, including associated details or properties.

For example, the test structure display image 74 can include a hierarchical breakdown, for example, by vehicle make 80, vehicle model 82, symptom type 84, vehicle component 86, and symptom 88. Each symptom 88 can be associated with a group of failure mode or disease or disorder tests 90 and preconditions 92. The symptom properties display image 78 can display properties or information stored by the dynamic diagnostic plan generator 10 regarding a specific symptom. For example, symptom properties can include a name or nametag 94 corresponding to the symptom, a code 96 corresponding to the symptom, a component identifier 98 and a symptom type identifier 100. The symptom properties can further include additional information, such as an introduction identifier 102, a priority 104, a key word 106, a description 108, and one or more flags 110 associated with the symptom.

The FMEA details editor display image 76 can display FMEA information stored by the dynamic diagnostic plan generator 10, such as statistical probability factors based on actual failure mode or disease or disorder occurrences corresponding to the symptom. For example, the FMEA information can include a nametag field 112, a name field 114, and a listing of records 116 associated with individual failure mode or disease or disorder tests. Each of the records can include, for example, a name tag 118, a component 120 associated with the failure mode or disease or disorder, a test identifier 122, an author rank assigning an estimated probability to the failure mode or disease or disorder test 124, a cost 126 associated with performing the failure mode or disease or disorder test, a risk 128 associated with the failure mode or disease or disorder test, a difficulty factor 130, or other information associated with the failure mode or disease or disorder test.

In operation, an expert diagnostic author can use an authoring work environment 72 to create a new failure mode or disease or disorder test. The author can define the system to which the failure mode or disease or disorder corresponds, for example, by specifying the vehicle make 80 and model 82 or race and age of the patient. The author can also specify the symptom type 84 or category, for example, a vehicle-defined symptom such as a diagnostic trouble code (DTC), a patient defined symptom such as high blood pressure or a user-defined symptom. The author can further define a pertinent system or unit 86 and a specific symptom 88 to be diagnosed.

The author can then define an introduction associated with the symptom to provide information about the symptom to the vehicle or medical technician. The introduction can include, for example, a failure mode or disease or disorder description, circuit diagrams, tips, or the like. In addition, the author can define multiple failure modes or disease or disorder 90 associated with the symptom. The author can create a reusable failure mode or disease or disorder test for each failure mode or disease or disorder and associate preconditions 92 required for each failure mode or disease or disorder test. Preconditions 92 can be procedures that must be completed prior to the performance of the failure mode or disease or disorder test, as previously discussed. Once created, a precondition 92 can be reused for additional failure mode or disease or disorder tests.

The author can further specify a sequence associated with the preconditions for a failure mode or disease or disorder test, an indication as to whether the precondition must be removed or reversed after the failure mode or disease or disorder test, and associated procedures for removing or reversing preconditions after the failure mode or disease or disorder test.

Figure 11:
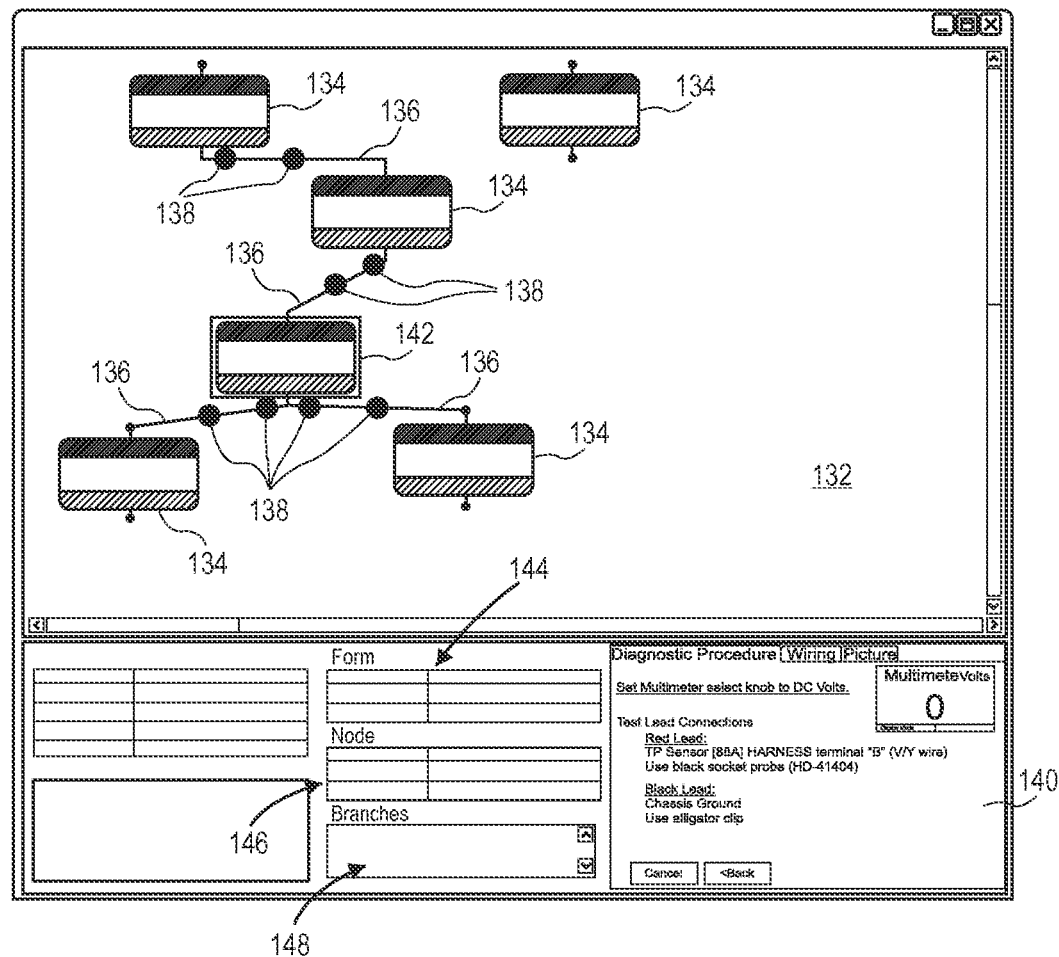
FIG. 11 illustrates a representative failure mode or disease or disorder test creation screen that can be prepared by the dynamic diagnostic plan generator for display on a display device.

FIG. 11 illustrates a representative display image of a failure mode or disease or disorder test creation display image 132 that an expert author can access, for example, by double-clicking on one of the failure modes or diseases or disorders 90 in the test structure display image 74 shown in FIG. 10. The failure mode or disease or disorder test creation display image 132 can include, for example, nodes 134 corresponding to diagnostic test procedure steps. The nodes 134 can be connected by decision branches 136 having round bulbs 138, which represent logical expressions associated with the test nodes 134 or decision branches 136. The failure mode or disease or disorder test creation display image 132 can further include a form 140 associated with a highlighted node 142. In addition, the failure mode or disease or disorder test creation display image 132 can provide form fields 144 for entering information about the form 140, node fields 146 for entering information about the highlighted node 142, and a branches field 148 for entering information about the branches 136 and logical expression bulbs 138 associated with the highlighted node 142.

In addition, in some embodiments, the dynamic diagnostic plan generator 10 can perform a reverse failure analysis that can identify symptoms, or operational problems, of a vehicle/power tool/patient and correlate each symptom to a specific failure mode of a vehicle/power tool disease or disorder of a patient component that is the cause of the symptom. An example of a method for reverse failure analysis for use with a vehicle diagnostic system is disclosed in a copending U.S. patent application, entitled "Reverse Failure Analysis Method and Apparatus for Diagnostic Testing," filed concurrently herewith by Fountain, et al. the disclosure of which is incorporated by reference in its entirety.

Furthermore, in some embodiments, the dynamic diagnostic plan generator 10 can gather and organize information corresponding to an optimized diagnostic test plan from a diverse set of information sources and generate an information object. The information object can be organized, for example, in a sequence or data structure that corresponds to the optimized diagnostic test plan. Thus, the information object can be interpreted as a dynamically-created manual that has been customized in accordance with a specific optimized diagnostic test plan, and which a user can access during execution of the corresponding diagnostic test plan, or at any time during diagnosis and repair, or treatment. An example of a method for generating an information object for use with a vehicle diagnostic system is disclosed in a copending U.S. patent application, entitled "Information Object Creation Based on an Optimized Test Procedure Method and Apparatus," filed concurrently herewith by Fountain, et al., the disclosure of which is incorporated by reference in its entirety.

Figure 12:
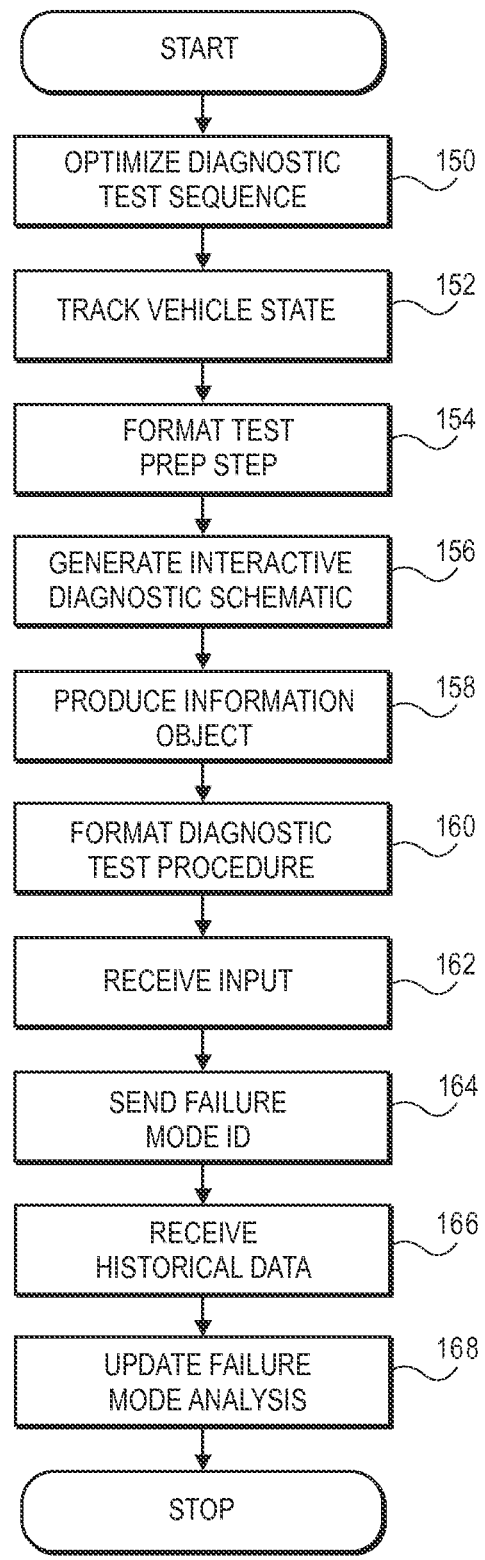
FIG. 12 is a flowchart illustrating steps that may be followed in accordance with one embodiment of the method or process of dynamically generating a diagnostic plan.

FIG. 12 illustrates a method or process for dynamically generating a diagnostic plan. The process can begin by proceeding to step 150, "Optimize Diagnostic Test Sequence," in which a sequence of diagnostic test procedures can be optimally ordered based on a failure mode or disease or disorder analysis, a vehicle or power tool history, a current vehicle or power tool state, user preferences, or other factors that can affect the resolution of a symptom or an operational problem of a vehicle or power tool, as described above. The diagnostic test sequence optimization can take into account information from a Failure Mode Effects Analysis (FMEA), as described above.

Next, in step 152, "Track Vehicle State," a current state of the vehicle or power tool can be read from a memory and updated, as explained above. Then, based on the diagnostic test sequence and vehicle or power tool state, in step 154, "Format Test Prep Step," a test preparation step or steps can be formatted for display on a display device to provide instructions for a vehicle or power tool technician, as described above.

In turn, an interactive diagnostic schematic can be generated in step 156, "Generate Interactive Diagnostic Schematic." As explained above, the interactive diagnostic schematic can illustrate a diagnostic test procedure when displayed on a display device. Subsequently, in step 158, "Produce Information Object," an information object can be created as a data structure containing information regarding the interactive diagnostic procedures as a supplemental resource for the vehicle or power tool technician.

In step 160, "Format Diagnostic Test Procedure," a diagnostic test procedure can be formatted for display on a display device to provide instructions for the vehicle or power tool technician, as described above. In addition, in step 162, "Receive Input," input can be received indicating that the test procedures have been performed and that the associated failure mode has been verified or eliminated, as described above.

Once the failure mode has been verified, in step 164, "Send Failure Mode," a failure mode identifier can be sent over a communication network to a central database, for example, at a service center or a manufacturer, as described above. Correspondingly, in step 166, "Receive Historical Data," historical data regarding actual failure mode occurrences can be received, for example, from a service center, regional database, a country database, a fleet database, or the like. Consequently, in step 168, "Update Failure Mode Analysis," failure mode frequency or rate information can be updated with the historical data for use in subsequent diagnostic test sequence optimizations.

Figure 13:
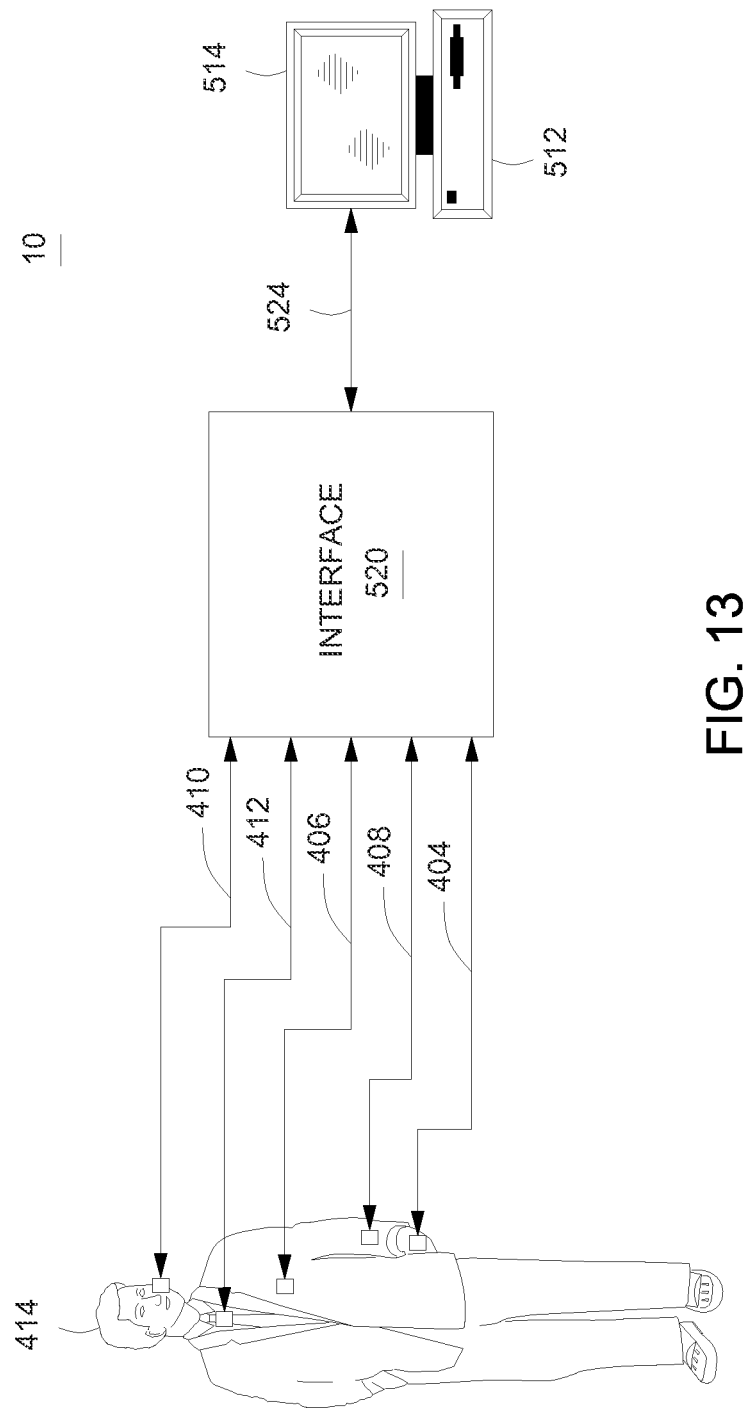
FIG. 13 is a patient test configuration in accordance with an embodiment of the present disclosure.

FIG. 13 illustrates a patient test configuration in accordance with an embodiment of the present disclosure. The dynamic diagnostic plan generator 10 can include a personal computer 512 with a display 514. In some embodiments, the dynamic diagnostic plan generator 10 can be coupled to a patient 414. The patient 414 may be monitored for various symptoms that may be related to various illnesses. For example, the dynamic diagnostic plan generator 10 can be coupled to the patient 414 by way of an interface 520, as shown in FIG. 13. The patient test configuration can further include electrical link 524, such as wires, cables, data buses, a communication network or a wireless communication link or network. The dynamic diagnostic plan generator 10 can display diagnostic test procedure instructions to a technician to aid in performing diagnostics of the patient 414. The dynamic diagnostic plan generator 10 can also receive feedback from the patient 414.

In an exemplary embodiment, the patient 414 may be coupled to an infrared finger cuff 404 to measure a saturated percentage of oxygen in the blood. Also, the patient 414 may be coupled to an electrocardiograph 406 that may illustrate the QRST waves of the heart. Further, the patient 414 may be coupled to a blood pressure transducer 408 that may measure the blood pressure. Furthermore, the patient 414 may be coupled to an adhesive pad containing a thermoelectric transducer 410 that may measure the body temperature. In addition, the patient 414 may be coupled to a thoracic transducer belt 412 that may measure airway respiratory rate. Additional monitoring devices may be coupled to the patient 414 to observe and collect various symptoms. These monitoring devices 404-412 may measure various symptoms of the patient 414 which are conveyed to the dynamic plan generator 10.

The dynamic diagnostic plan generator 10 can verify a current condition of the patient 414 with regard to a specific precondition, or a group of current conditions corresponding to a number of preconditions. If a precondition is required for the subsequent test procedure and the corresponding patient 414 condition is currently not valid, the test preparation step formatter 22 can format a test preparation step for display on the display device 34 to instruct the medical technician to set up the required precondition or patient test configuration.

As an example, FIG. 14 illustrates a representative test preparation step display screen 40 that can be prepared by the test preparation step formatter 22 to instruct the medical technician on the steps for coupling the patient 414 to an electrocardiograph 406. As shown in FIG. 14, the pulse of the patient 414 may be recorded, the body temperature of the patient may be recorded, the electrocardiogram may be performed, a complete blood count may be initiated and the lung condition of the patient 414 may be evaluated. In this manner, the QRST waves of the heart of the patient 414 may be read. Of course, if the precondition is required for the subsequent test procedure and the corresponding patient condition is currently valid, the test preparation step formatter 22 may elect not to format a test preparation step for display.

In addition, the dynamic diagnostic plan generator 10 can receive feedback indicating when the precondition has been satisfied. For example, the dynamic diagnostic plan generator 10 can receive a data signal from the interface 520 indicating that the precondition has been satisfied. In some embodiments, the dynamic diagnostic plan generator 10 can receive a feedback signal from test equipment, such as the electrocardiograph 406 coupled to the patient 414. Similarly, the dynamic diagnostic plan generator 10 can receive user input from the medical technician by way of the input/output device 16 indicating that the precondition has been satisfied, or that the medical technician has complied with the test preparation step instructions.

Once the precondition has been satisfied, the dynamic diagnostic plan generator 10 can update the patient condition, for example, in a memory register, to reflect a valid setting corresponding to the precondition. Thus, the patient condition can be continually updated to maintain a current and accurate patient condition that is available to the diagnostic system at any time in order to determine test preparation steps required to prepare the patient 414 between diagnostic procedures in a diagnostic test sequence.

In the case that the patient condition is currently valid but is not required for a subsequent test procedure, the test preparation step formatter 22 can format a test preparation step for display instructing the medical technician to reverse, or undo, the patient condition. Correspondingly, the dynamic diagnostic plan generator 10 can receive feedback as described above indicating that the condition has been reversed, and can update the patient condition, for example, in a memory register, to reflect an invalid setting corresponding to the condition, or precondition.

The dynamic diagnostic plan generator 10 can maintain patient condition for any number of preconditions associated with the diagnostic test procedures which can be configured to be readily available for use, or reuse, with any existing test procedure or with a new test procedure. For example, preconditions can include, but are not limited to, any of the following:
  time since last meal
  time since last drink
  body temperature
  seated position
  standing position
  heart rate
  a test equipment connection
  breath volume
  an ambient air temperature
  pace on a treadmill test
  oxygenation level of blood
  reflex response
  consciousness
  allergies
  phobias
  medical history
  prior surgeries
  current medications, or
  time of day.

Figure 16:
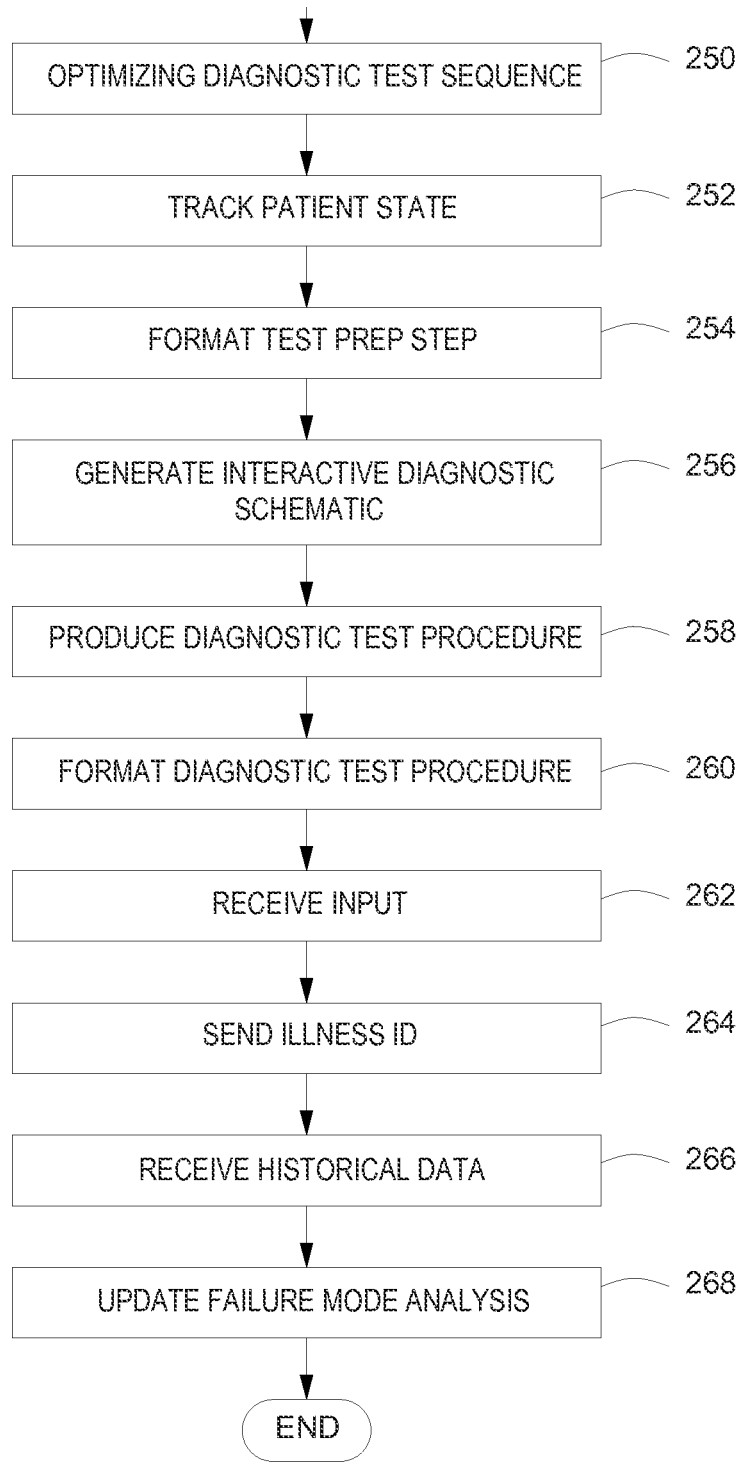
FIG. 16 is a flowchart illustrating a method or process for dynamically generating a diagnostic plan for a patient according to an embodiment of the present disclosure.

FIG. 16 illustrates a method or process for dynamically generating a diagnostic plan according to another embodiment of the present disclosure. The process can begin by proceeding to step 250, "Optimize Diagnostic Test Sequence," in which a sequence of diagnostic test procedures can be optimally ordered based on a failure mode or disease or disorder analysis, a patient's history, a current patient state, user preferences, or other factors that can affect the resolution of a symptom or an illness of a patient. The diagnostic test sequence optimization can take into account information from a Failure Mode Effects Analysis (FMEA), as described above. For example, the sequence can be optimized in accordance with, for example, a priority input by a diagnostic test procedure author, a user preference input and any combination of the failure mode or disease or disorder analysis factors. Thus, the diagnostic test sequence optimizer 18 (shown in FIG. 2) is highly configurable to allow customization of the sequence optimization process. In another exemplary embodiment, the historical failure mode or disease or disorder data can be used by the diagnostic test sequence optimizer 18 to order the diagnostic test procedures in an optimal sequence based on the latest updated information available. As a result, the diagnostic test sequence compiled by the dynamic diagnostic plan generator 10 (shown in FIG. 2) can change over time in a dynamic manner, based on actual failure mode or disease or disorder occurrences.

Next, in step 252, "Track Patient State," a current state of the patient can be read from a memory and updated. For example, the patient's record may be inputted by a user. In another exemplary embodiment, the patient's record may be collected from a database storing the patient records. Then, based on the diagnostic test sequence and patient state, in step 254, "Format Test Prep Step," a test preparation step or steps can be formatted for display on a display device to provide instructions for a technician, as described above.

In turn, an interactive diagnostic schematic can be generated in step 256, "Generate Interactive Diagnostic Schematic." As explained above, the interactive diagnostic schematic can illustrate a diagnostic test procedure when displayed on a display device. For example, the interactive diagnostic schematic 64 (shown in FIG. 9) can illustrate any number of patient organs. For example, the organs could represent a heart, a lung, a liver, a kidney, a stomach, a colon, a brain, and a respiratory system, or any additional organs related to a diagnostic procedure. Subsequently, in step 258, "Produce Information Object," an information object can be created as a data structure containing information regarding the interactive diagnostic procedures as a supplemental resource for the diagnostic technician or doctor diagnosing illnesses.

In step 260, "Format Diagnostic Test Procedure," a diagnostic test procedure can be formatted for display on a display device to provide instructions for the diagnostic technician or doctor, as described above. In addition, in step 262, "Receive Input," input can be received indicating that the test procedures have been performed and that the associated failure mode or disease or disorder has been verified or eliminated, as described above.

Once the failure mode or disease or disorder has been verified, in step 264, "Send Illness ID," an illness identifier can be sent over a communication network to a central database, for example, at a medical center or a central database. For example, the illness identifier can be sent to a central database for storing. Correspondingly, in step 266, "Receive Historical Data," historical data regarding actual illness occurrences can be received, for example, from a medical center, regional database, a country database, a medical database, or the like. Consequently, in step 268, "Update Failure Mode or Disease or Disorder Analysis," failure mode or disease or disorder frequency or rate information can be updated with the historical data (e.g., illness frequency or rate) for use in subsequent diagnostic test sequence optimizations.

Some of the figures are block diagrams and flowcharts of methods, apparatuses and computer program products according to various embodiments of the present invention. It will be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus according to the present invention can include other means, such as hardware or some combination of hardware and software, including one or more processors or controllers, for performing the disclosed functions.

In this regard, FIG. 2 depicts the apparatus of one embodiment including several of the key components of a general-purpose computer by which an embodiment of the present invention may be implemented. Those of ordinary skill in the art will appreciate that a computer can include many more components than those shown in FIG. 2. However, it is not necessary that all of these generally conventional components be shown in order to disclose an illustrative embodiment for practicing the invention. The general-purpose computer can include a processing unit 12 and a system memory 14, which may include random access memory (RAM) and read-only memory (ROM). The computer also may include nonvolatile storage memory, such as a hard disk drive, where additional data can be stored.

An embodiment of the present invention can also include one or more input or output devices 16, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

Typically, computer program instructions may be loaded onto the computer or other general purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touchscreen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

The many features and advantages of the invention are apparent from the detailed specification, and thus, it is intended by the appended claims to cover all such features and advantages of the invention, which fall within the true spirit, and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A computer-implemented method of dynamically producing a diagnostic test procedure sequence to diagnose a disease or disorder of a patient, comprising:

receiving disease or disorder historical data over a communication network from a central database;

updating disease or disorder analysis based on the historical data;

selecting a first plurality of diagnostic test procedures related to a symptom exhibited by the patient;

arranging an order of the first plurality of diagnostic test procedures based on a probabilistic disease or disorder analysis and time required to perform each of the first plurality of diagnostic test procedures;

formatting a step of a first diagnostic test procedure from among the first plurality of diagnostic test procedures for display on a display device;

displaying the formatted step on the display device;

arranging an order of a second plurality of diagnostic test procedures, which includes one diagnostic test procedure of the first plurality of diagnostic test procedures, during execution of the first plurality of diagnostic test procedures, and based on intermediate diagnostic test information obtained from execution of the first diagnostic test procedure, wherein arranging the order of the second plurality of diagnostic test procedures is based at least in part on the updated disease or disorder analysis; and displaying a step of a second diagnostic test procedure from among the second plurality of diagnostic test procedures on the display device, wherein each of the above steps is performed by a computer.

2. The computer-implemented method of claim 1, wherein formatting comprises preparing a graphical user interface whereby a user performs direct manipulation of displayed graphical representations of objects and symbols by way of an input device.

3. The computer-implemented method of claim 1, further comprising tracking a state of the patient.

4. The computer-implemented method of claim 3, further comprising formatting a test preparation step required for the first diagnostic test procedure based on the tracked patient state for display on the display device.

5. The computer-implemented method of claim 1, further comprising generating an interactive diagnostic schematic to illustrate the first diagnostic test procedure.

6. The computer-implemented method of claim 1, further comprising producing an information object based on the diagnostic test procedure sequence.

7. The computer-implemented method of claim 1, further comprising:
   receiving an input indicating that the disease or disorder has been diagnosed; and
   sending a disease or disorder identifier representing the disease or disorder over the communication network to the central database.

8. A diagnostic tool for dynamically producing a diagnostic test sequence to diagnose a disease or disorder of a patient, comprising:
   a processor configured to produce the diagnostic test sequence;
   a display device in communication with the processor;
   a memory storing software modules that when executed:
   receive disease or disorder historical data over a communication network from a central database;
   update disease or disorder analysis based on the historical data;
   select a first plurality of diagnostic test procedures related to a symptom exhibited by the patient;
   arrange an order of a first plurality of diagnostic test procedures based on a probabilistic disease or disorder analysis and time required to perform each of the first plurality of diagnostic test procedures;
   format a step of a first diagnostic test procedure from among the first plurality of diagnostic test procedures for display on the display device;
   displaying the formatted step on the display device;
   arrange an order of a second plurality of diagnostic test procedures, which includes one diagnostic test procedure of the first plurality of diagnostic test procedures, during execution of the first plurality of diagnostic test procedures, and based on intermediate diagnostic test information obtained from execution of the first plurality of diagnostic test procedures, wherein arranging the order of the second plurality of diagnostic test procedures is based at least in part on the updated disease or disorder analysis; and
   format a step of a second diagnostic test procedure from among the second plurality of diagnostic test procedures for display on the display device.

9. The diagnostic tool of claim 8, further comprising:
   a patient state tracker for tracking a state of the patient; and
   a test procedure formatter for formatting a test preparation step required for the first diagnostic test procedure based on the tracked patient's state for display on the display device.

10. The diagnostic tool of claim 8, further comprising a diagnostic schematic generator for generating an interactive diagnostic schematic to illustrate the first diagnostic test procedure.

11. The diagnostic tool of claim 8, further comprising an information object producer for producing an information object based on the diagnostic test sequence.

12. The diagnostic tool of claim 8, further comprising:
   an input module for receiving an input indicating that the disease or disorder has been diagnosed; and
   a disease or disorder identifier sender for sending a disease or disorder identifier representing the disease or disorder over the communication network to the central database.

13. The diagnostic tool of claim 8, further comprising:
   a historical data receiver for receiving disease or disorder historical data over the communication network from the central database; and
   an updating module for updating the disease or disorder analysis based on the historical data.

14. A computer-implemented method of producing a diagnostic test sequence to diagnose a disease or disorder of a patient executed by a diagnostic tool, comprising:
   arranging an order of a first plurality of diagnostic test procedures related to the disease or disorder identified for the patient, wherein arranging is based on a statistical probability information and time required to perform each of the first plurality of diagnostic test procedures;
   formatting a step of a first diagnostic test procedure from among the first plurality of diagnostic test procedures for display on a display device;
   displaying the formatted step on the display device;
   arranging an order of a second plurality of diagnostic test procedures, which includes one diagnostic test procedure of the first plurality of diagnostic test procedures, during execution of the first plurality of diagnostic test procedures, and based on intermediate diagnostic test information obtained from execution of the first plurality of diagnostic test procedures, wherein the intermediate diagnostic test information comprises new information derived from a particular diagnostic test procedure when the first plurality of diagnostic test procedures do not result in a final diagnosis; and
   displaying a step of a second diagnostic test procedure from among the second plurality of diagnostic test procedures on the display device,
   wherein each of the above steps is performed by a computer.

15. The computer-implemented method of claim 14, wherein the statistical probability information comprises a probabilistic disease or disorder analysis based on historical outcomes of actual diagnostic testing.

16. The computer-implemented method of claim 14, wherein the intermediate diagnostics test information comprises information of an interrelation of two or more symptoms.

17. The computer-implemented method of claim 14, wherein the intermediate diagnostic test information comprises a result of a particular diagnostic test procedure or a result of a combination of the first plurality of diagnostic test procedures.

18. The computer-implemented method of claim 14, wherein arranging the order of the first plurality of diagnostic test procedures further comprises adding a new diagnostic test procedure to the first plurality of diagnostic test procedures, or removing an existing diagnostic test procedure from the first plurality of diagnostic test procedures.

19. The computer-implemented method of claim 14, further comprising:
- tracking a current state of the patient during and between diagnostic test procedures;
- determining a set of preconditions or patient test configuration requirements necessary for an individual diagnostic test procedure; and
- providing a diagnostic test preparation step to reconfigure the patient between diagnostic test procedures.

20. The computer-implemented method of claim 14, further comprising analyzing comparative utility among the first plurality of diagnostic test procedures.

\* \* \* \* \*